United States Patent
Persson et al.

(10) Patent No.: US 11,530,438 B2
(45) Date of Patent: Dec. 20, 2022

(54) HIGHLY SPECIFIC CIRCULAR PROXIMITY LIGATION ASSAY

(71) Applicant: The Board of Trustees of the Leland Stanford Junior University, Stanford, CA (US)

(72) Inventors: Henrik H. J. Persson, Palo Alto, CA (US); Roxana Jalili, Palo Alto, CA (US); Joseph L. Horecka, Stanford, CA (US); Ronald W. Davis, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 355 days.

(21) Appl. No.: 16/483,383

(22) PCT Filed: Feb. 20, 2018

(86) PCT No.: PCT/US2018/018859
§ 371 (c)(1),
(2) Date: Aug. 2, 2019

(87) PCT Pub. No.: WO2018/160397
PCT Pub. Date: Sep. 7, 2018

(65) Prior Publication Data
US 2019/0360025 A1    Nov. 28, 2019

Related U.S. Application Data

(60) Provisional application No. 62/465,320, filed on Mar. 1, 2017.

(51) Int. Cl.
*C12Q 1/6816* (2018.01)
*C12Q 1/6851* (2018.01)

(52) U.S. Cl.
CPC ......... *C12Q 1/6816* (2013.01); *C12Q 1/6851* (2013.01); *C12Q 2521/501* (2013.01); *C12Q 2523/307* (2013.01); *C12Q 2531/125* (2013.01); *C12Q 2537/162* (2013.01); *C12Y 605/01* (2013.01)

(58) Field of Classification Search
CPC ............... C12Q 1/6816; C12Q 1/6851; C12Q 2521/501; C12Q 2521/319; C12Q 2523/307; C12Q 2525/307; C12Q 2531/125; C12Q 2537/143; C12Q 2537/162; C12Q 2533/107; C12Y 605/01
See application file for complete search history.

(56) References Cited

U.S. PATENT DOCUMENTS

| | | |
|---|---|---|
| 2004/0248103 A1 | 12/2004 | Feaver et al. |
| 2011/0223585 A1 | 9/2011 | Gullberg et al. |
| 2014/0170654 A1 | 6/2014 | Landegren et al. |
| 2014/0194311 A1 | 7/2014 | Gullberg et al. |

FOREIGN PATENT DOCUMENTS

| | | |
|---|---|---|
| JP | 2005-508495 | 3/2005 |
| JP | 2009-529904 | 8/2009 |
| WO | WO2012152942 A1 | 11/2012 |
| WO | WO 2016/168612 | 10/2016 |

OTHER PUBLICATIONS

Extended European Search Opinion for European Application No. EP18760612.4, dated Oct. 6, 2020 (7 pages).
Chang et al., "Identification of a biomarker panel using a multiplex proximity ligation assay improves accuracy of pancreatic cancer diagnosis", Journal of Translational Medicine, 2009, 7:105.
Fredriksson et al., "Protein detection using proximity-dependent DNA ligation assays", Nature Biotechnology, May 2002, 20: 473-477.
Fredriksson et al., "Multiplexed protein detection by proximity ligation for cancer biomarker validation", Nature Methods, Apr. 2007, 4(4): 327-329.
Fredriksson et al., "Multiplexed Proximity Ligation Assays to Profile Putative Plasma Biomarkers Relevant to Pancreatic and Ovarian Cancer", Clinical Chemistry, 2008, 54(3): 582-589.
Gullberg et al., "Cytokine detection by antibody-based proximity ligation", PNAS, 2004, 101(22): 8420-8424.
Jalili et al., "Streamlined circular proximity ligation assay provides high stringency and compatibility with low-affinity antibodies", PNAS, Jan. 16, 2018, E925-E933.
Koos et al., "Analysis of Protein Interactions in situ by Proximity Ligation Assays", Microbiology and Immunology, 2013, DOI: 10.1007/82_2013_334.
Lundberg et al., "Multiplexed Homogeneous Proximity Ligation Assays for High-throughput Protein Biomarker Research in Serological Material*", Molecular & Cellular Proteomics 10.4, Technological Innovation and Resources, 2011, 11 pages.
Nam et al., "Nanoparticle-Based Bio—Bar Codes for the Ultrasensitive Detection of Proteins", Science, Sep. 26, 2003, 301:1884-1886.
Sano et al., "Immuno-PCR: Very Sensitive Antigen Detection by Means of Specific Antibody-DNA Conjugates", Scienc, Oct. 2, 1992, 258: 120-122.

(Continued)

*Primary Examiner* — David C Thomas
(74) *Attorney, Agent, or Firm* — Casimir Jones, S.C.; Kelly A. Barton

(57) ABSTRACT

Provided herein is a circular proximity ligation assay in which proximity-probes are employed as bridges to connect two free oligonucleotides via a dual ligation event, resulting in the formation of a circle. The circles are then quantified by, e.g., qPCR. The addition of an extra oligonucleotide is believed to enhance specificity by decreasing the probability of random background ligation events. In addition, circle formation may have selective advantages, as uncircularized DNA can be removed by a simple exonuclease treatment and it has streamlined the workflow by eliminating preamplification prior to qPCR.

12 Claims, 13 Drawing Sheets
Specification includes a Sequence Listing.

(56) References Cited

OTHER PUBLICATIONS

Schweitzer et al., "Multiplexed protein profiling on microarrays by rolling-circle amplification", Nat Biotechnol., Apr. 2002, 20(4): 359-365.
Shah et al., "Barriers to transmission of transcriptional noise in a c-fos c-jun pathway", Molecular Systems Biology, 2013, 9:687.
Tate et al., "Interferences in Immunoassay", Clin Biochem Rev, May 25, 2004, 25: 105-120.
Xie et al., "Development of a dual aptamer-based multiplex protein biosensor", Biosens Bioelectron., Aug. 15, 2010, 25(12): 2663-2668.
Jalili et al., "Streamlined circular proximity ligation assay provides high stringency and compatibility with low-affinity antibodies." Proc Natl Acad Sci U S A. Jan. 30, 2018;115(5): E925-E933.
Schwenk et al., "Toward Next Generation Plasma Profiling via Heat-induced Epitope Retrieval and Array-based Assays*" Mol Cell Proteomics. Nov. 2010; 9(11): 2497-507.
Anderson et al., "The Human Plasma Proteome: History, Character, and Diagnostic Prospects" Molecular & Cellular Proteomics 2002, 1: 845-867.
Landegren et al., "Opportunities for Sensitive Plasma Proteome Analysis" Anal. Chem. 2012, 84: 1824-1830.
Stenken et al., "Bioanalytical Chemistry of Cytokines—A Review" Anal Chem Acta. Jan. 1, 2015; 853: 95-115.
Office Action for JP 2019-543321, dated Aug. 22, 2022, 3 pages.

HIGHLY SPECIFIC CIRCULAR PROXIMITY LIGATION ASSAY

CROSS-REFERENCING

This application is a § 371 national phase of International Application No. PCT/US2018/018859, filed on Feb. 20, 2018, which claims the benefit of U.S. provisional application Ser. No. 62/465,320, filed on Mar. 1, 2017, which applications are incorporated by reference herein.

GOVERNMENT RIGHTS

This invention was made with Government support under contract HG000205 awarded by the National Institutes of Health. The Government has certain rights in the invention.

BACKGROUND

Quantitative detection of protein biomarkers in biological fluids is essential for diagnosis, monitoring and personalized treatment of disease. Despite considerable progress in recent years the clinical use of validated proteomic biomarkers remains limited (1). The benchmark for affinity-based protein measurements is defined by the enzyme-linked immunosorbent assay (ELISA) where affinity ligands (e.g. antibodies) are used in a sandwich format to detect and quantify the protein of interest (2, 3). ELISA generally involves several steps starting with sample incubation where the target analyte is captured on a surface precoated with primary antibodies, followed by washing steps and recognition with a secondary antibody, which facilitates detection with a colorimetric, fluorescent or luminescent label. ELISA offers reasonable sensitivity but requires a large sample volume, has limited dynamic range and frequently suffers from false positives due to nonspecific binding (4, 5). These limitations interfere with the discovery and validation of novel biomarker candidates that have the potential to enable early diagnosis and regular molecular monitoring of disease.

Immunoassays combined with nucleic acid-based amplification and detection have facilitated new approaches and have extended the analytical sensitivity beyond that achievable with ELISA (6-9). One particularly promising approach is the proximity ligation assay (PLA) (10, 11). In PLA, pairs of affinity probes are individually conjugated to short, single-stranded DNA molecules to form proximity-probes that carry either a phosphorylated 5'-end or a 3'-hydroxyl group. When the probe pairs subsequently bind to their cognate target analyte in solution, the associated DNA strands are brought into close proximity and aligned by hybridization to a third bridging oligonucleotide. The free DNA ends are ligated, forming a new DNA sequence that is amplified and quantified using quantitative PCR (qPCR). It has previously been demonstrated that PLA provides femtomolar sensitivity and a wide dynamic range over 5 orders of magnitude, consuming as little as 1 µL of sample (12). One key benefit of PLA is that it addresses the widespread problem of cross-reactivity in antibody-based protein detection. Potential signals from cross-reactive antibodies are eliminated by tailoring the DNA sequences such that ligation only takes place when cognate proximity-probes are bound to the target analyte. This technology has been applied to detect more than 20 different biomarkers in clinical plasma samples using panels of seven multiplex PLA reactions (13, 14). Others have expanded the multiplexing capability even further (15).

One of the limitations of affinity-based immunoassays, including PLA, is the so called hook effect in which the signal decreases at high antigen concentrations resulting in incorrectly low signals or even false negatives (16). The hook effect becomes predominant when the analyte concentration exceeds the concentration of proximity-probes (>>1 nM) and it effectively determines the upper quantification limit (17). The proximity-probe concentration can potentially be increased, but must be carefully balanced against a deteriorating signal-to-noise ratio from random background ligation events when probes and the bridge oligo come together by chance. The hook effect can ordinarily be avoided by sample dilution; however, dilution alters binding equilibrium. This does not present a problem for high affinity interactions but it may prevent low affinity antibodies to bind to their target analytes, thereby limiting the effectiveness of PLA to high-affinity capture agents (18). While incompatibility with low-affinity antibodies is a major drawback for PLA, it is not restricted to this assay alone. The availability of high affinity antibodies or other capture reagents is a general limitation for all sandwich immunoassays because the sensitivity is ultimately determined by the quality of the reagents used (19).

Numerous approaches have been developed to improve PLA performance including concentration of minute amounts of analyte on a solid-phase prior to ligation (10, 18, 20), use of multivalent proximity-probes (21), addition of multiple affinity probes (22, 23), special design of asymmetric bridge oligos (17), inclusion of protecting oligonucleotides prehybridized to proximity-probes in order to reduce background ligation events (22, 24), and the use of novel amplification schemes (25-28). Some of the amplification schemes entail enzymatic manipulations where the ligation products are released from antibodies and converted into circles used for isothermal rolling circle amplification (26, 29-31). Many of these approaches have improved assay reproducibility, although precision still remains a challenge for adaptation into clinical diagnostics.

As such, there is a need for new assays for detecting analytes in a sample, particularly assays that can use lower affinity binding reagents.

SUMMARY

Provided herein, among other things, is a circular proximity ligation assay in which proximity-probes are employed as bridges to covalently join two free oligonucleotides via a dual ligation event, resulting in the formation of a circle. The circles are then quantified by, e.g., qPCR. In some embodiments, the method may comprise: incubating a sample comprising a target analyte with: (i) a first conjugate comprising a binding agent and first splint oligonucleotide, and (ii) a second conjugate comprising a binding agent and a second splint oligonucleotide, under conditions suitable for binding of the binding agents of the first and second conjugates to the target analyte, to produce a product, incubating at least some of the product with: (i) a set of probes that produces a ligatable circle only when the probes are hybridized to the first and second splint oligonucleotides; and (ii) a ligase, to produce a reaction mix comprising covalently closed circular molecules, treating at least some of the reaction mix with an exonuclease to terminate the ligation and degrade any nucleic acid that is not a covalently closed circular molecule; and, after the exonuclease treatment, quantifying the amount of covalently closed circular molecules produced in the ligation step. A kit for performing the method is also provided.

Relative to other methods, the addition of an extra oligonucleotide is believed to enhance specificity by decreasing the probability of random background ligation events. In addition, circle formation has selective advantages, as uncircularized DNA can be removed by a simple exonuclease treatment and it has streamlined the workflow by eliminating preamplification prior to qPCR. As a result, this assay is believed to be much more straightforward than not only prior assays, but most existing protein detection methods, and can be performed in a single reaction tube with a tiny sample volume (e.g., 2 uL). The assay format can utilize the same proximity-probes as used in traditional proximity ligation assays, which enables a direct performance comparison between the two methods. Moreover, it has been demonstrated that the enhanced specificity in this assay can be used to increase proximity-probe concentration while maintaining a low probability of background ligation events. This results in a better signal-to-noise ratio, improved assay performance and provides a path for compatibility with low affinity reagents without the need for pre-concentration on solid-phase.

Quantitative detection of protein biomarkers over a wide concentration range from minute amounts of blood is essential for clinical diagnostics. Proximity ligation assay combines antibody-oligo conjugates, enzymatic ligation and PCR amplification into a sensitive method for quantitative protein detection from small volumes. The method herein describes a streamlined and more stringent assay format that takes advantage of DNA circle formation to remove unwanted DNA molecules. Kinetic analysis of antibody-antigen interactions demonstrates that variation in assay performance between various biomarkers is an effect of antibody quality. It has been shown that this new assay format enables compatibility with low affinity reagents, a major limitation for most protein quantitation methods, while improving sensitivity and reproducibility.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
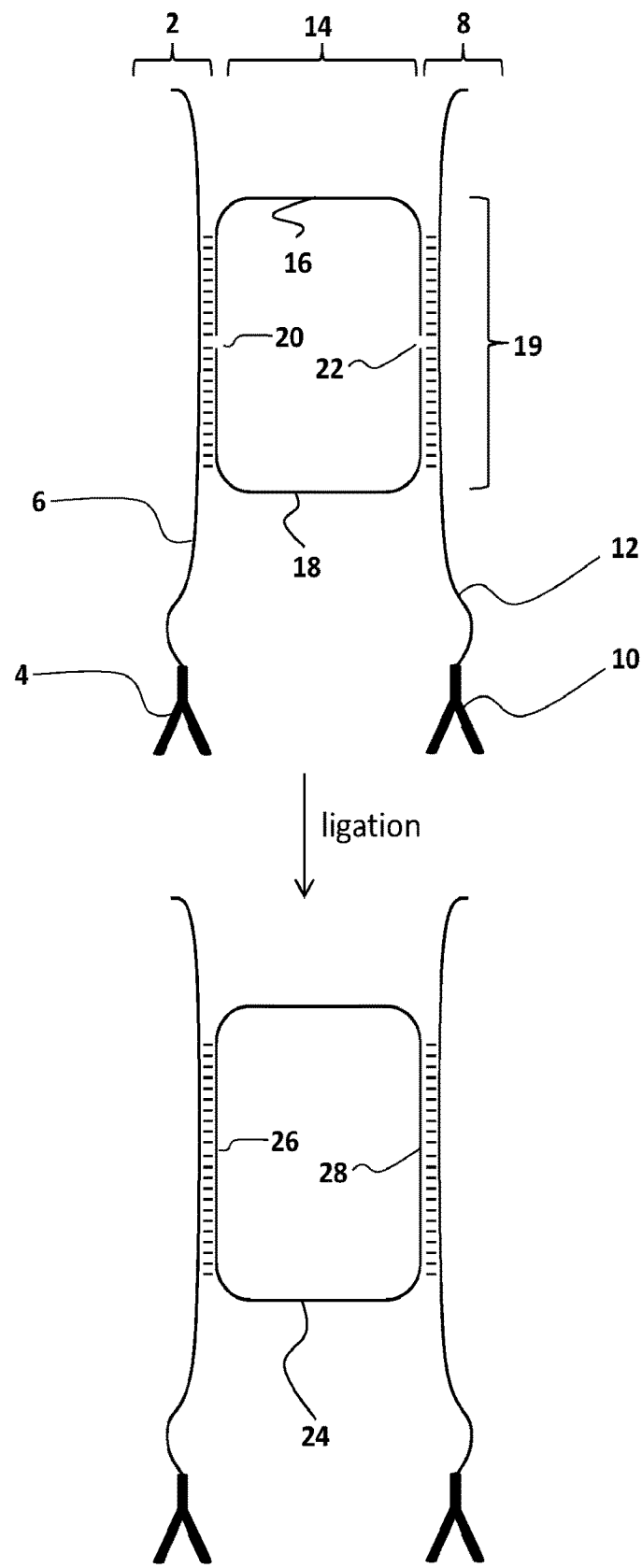
FIG. 1. Schematic illustration of some of the features of the probe system used herein.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" refers to a sample of organic material from a biological source and, as such, may comprise protein, nucleic acid, carbohydrates, small molecules, etc. A sample may be from an animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "specific binding" refers to the ability of a binding reagent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

The term "affinity" refers to the strength of binding between two entities. The affinity between two proteins (e.g., a capture agent and an analyte) when they are specifically bound together in a capture agent/analyte complex may be characterized by a $K_D$ (equilibrium dissociation constant) of less than $10^{-6}$ M, less than $10^{-7}$ M, less than $10^{-8}$ M, less than $10^{-9}$ M, less than $10^{-10}$ M, less than $10^{-11}$ M, or less than about $10^{-12}$ M.

The term "epitope" as used herein is defined as a site in an antigen molecule that is bound by an antibody or non-antibody scaffold. An antigen can have one or more epitopes. In some cases, an epitope can be a linear sequence of at least five amino acids. In some cases, an antibody will only bind to an antigen molecule if the epitope has a specific three-dimensional structure.

A "subject" of diagnosis or treatment is a plant or animal, including a human. Non-human animals subject to diagnosis or treatment include, for example, livestock and pets.

As used herein, the term "incubating" refers to maintaining a sample and binding agent under conditions that are suitable for specific binding of the binding agent to molecules in the sample. Such conditions typically include a period of time, a temperature, and an appropriate binding buffer (e.g., PBS or the like). Such conditions are well known for antibodies, aptamers, and other binding agents.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides, ribonucleotides or a combination thereof, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as an inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example. Oligonucleotides can have nucleotide analogs and, in some embodiments, at least some of the linkages between the nucleotides do not need to be phosphate. In some embodiments, an oligonucleotide can have a phosorothioate linkage, particularly at the 3' end and/or 5' end of the oligonucleotide.

The term "primer" as used herein refers to an oligonucleotide that is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

The term "binding agents" refers to any member of a pair of molecules that specifically bind to each other. For example, an antibody (a type of capture agent) binds to an antigen. In this example, both the antibody and the antigen can be a binding agent. The complex that contains a pair of binding agents contains a capture agent (e.g., an antibody or a non-antibody scaffold) and a moiety that is not a capture agent, e.g., a protein, a metabolite, small molecule, carbohydrate, drug, etc.

The term "capture agent" refers to proteins that have a domain that specifically binds to other moieties. For example, antibodies and non-antibody binding scaffolds that have the ability to specifically bind to another moiety. Non-antibody binding proteins include aptamers and non-antibody proteins such as those described in Binz et al. (Curr Opin Biotechnol. 2005 16:459-69), Binz et al. (Nat. Biotechnol. 2005 23:1257-68), Forrer et al. (Chembiochem. 2004 5:183-9), Gronwall et al. (J. Biotechnol. 2009 140: 254-69), Hosse et al. (Protein Sci. 2006 15:14-27) and Skerra et al. (Curr. Opin. Biotechnol. 2007 18:295-304), which are incorporated by reference herein.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, polyclonal antibodies (which may or may not be affinity purified), monoclonal antibodies, and fusion proteins comprising an antigen-binding portion of an antibody and a non-antibody protein. This term encompasses by antibody fragments (e.g., Fab', Fv, F(ab')$_2$ etc.) that retain specific binding to antigen. An antibody may be monovalent or bivalent.

A nucleic acid is considered to be "selectively hybridizable" to a nucleic acid sequence if the two sequences specifically hybridize to one another under moderate to high stringency hybridization and wash conditions. Moderate and high stringency hybridization conditions are known (see, e.g., Ausubel et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "ligating", as used herein, refers to the enzymatically catalyzed joining of the terminal nucleotide at the 5' end of a first nucleic acid molecule to the terminal nucleotide at the 3' end of a second nucleic acid molecule.

The terms "plurality", "set" and "population" are used interchangeably to refer to something that contains at least 2 members. In certain cases, a plurality may have at least 10, at least 100, at least 100, at least 10,000, at least 100,000, at least $10^6$, at least $10^7$, at least $10^8$ or at least $10^9$ or more members.

The term "strand" as used herein refers to a nucleic acid made up of nucleotides covalently linked together by covalent bonds, e.g., phosphodiester bonds.

The term "covalently linking" refers to the production of a covalent linkage between two separate molecules. Ligation produces a covalent linkage.

As used herein, the term "ligatably adjacent" in the context of two oligonucleotide sequences that are ligatably adjacent to one another, means that there are no intervening nucleotides between two oligonucleotides and they can be ligated to one another.

As used herein, the term "splint oligonucleotide," as used herein, refers to an oligonucleotide that, when hybridized to two or more other polynucleotides, acts as a "splint" to position the 5' and 3' ends of two other polynucleotides next to one another so that they can be ligated together, as illustrated in FIG. 1.

The terms "ligatable circle" and "ligatable circular complex" refer to a circular complex in which the various oligonucleotides are ligatably adjacent to one another in a circle, held together by splint oligonucleotides, as illustrated in FIG. 1.

As used herein, the term "a set of probes that produces a ligatable circle only when the probes are hybridized to first and second splint oligonucleotides" comprises a pair of probes that (a) contains ends that hybridize to different splint oligonucleotides (i.e., a first splint oligonucleotide and a second splint oligonucleotide) and (b) hybridize to the first and second splint oligonucleotides to form a ligatable circle. In a complex comprising a first probe molecule and a second probe molecule, the 5' end of the first probe molecule is ligatably adjacent to the 3' end of the second probe molecule and the 3' end of the first probe molecule is ligatably adjacent to the 5' end of the second probe molecule. In this example, two ligation events are required for circularization. The term "only" in this phrase is intended to mean that the probes do not produce a ligatable circle if they are hybridized to only one of the first and second splint oligonucleotides (i.e., only one but not the other). A set of "probes that produces a ligatable circle only when the probes are hybridized to the first and second splint oligonucleotides" is illustrated in FIG. 1.

As used herein, the term "covalently closed circular molecule" refers to a strand that is in the form of a closed circle that has no free 3' or 5' ends.

The term "corresponds to" and grammatical equivalents, e.g., "corresponding", as used herein refers to a specific relationship between the elements to which the term refers. For example, an RCA product corresponds to an analyte if the RCA product can be used to quantify that analyte in a sample.

As used herein, the term "rolling circle amplification" or "RCA" for short refers to an isothermal amplification that generates linear concatemerized copies of a circular nucleic acid template using a strand-displacing polymerase. RCA is well known in the molecular biology arts and is described in a variety of publications including, but not limited to Lizardi et al. (Nat. Genet. 1998 19:225-232), Schweitzer et al. (Proc. Natl. Acad. Sci. 2000 97:10113-10119), Wiltshire et al. (Clin. Chem. 2000 46:1990-1993) and Schweitzer et al. (Curr. Opin. Biotech 2001 12:21-27), which are incorporated by reference herein. This term includes linear RCA as well as exponential RCA (which can use random primers in some cases).

As used herein, the term "rolling circle amplification products" refers to the concatemerized products of a rolling circle amplification reaction.

As used herein, the term "counting" refers to determining the number of individual objects in a greater collection. "Counting" requires detecting separate signals from individual objects in a plurality (not a collective signal from the plurality of objects) and then determining how many objects there are in the plurality by counting the individual signals. In the context of the present method, "counting" is done by determining the number of individual signals in an array of signals.

Other definitions of terms may appear throughout the specification.

DESCRIPTION OF EXEMPLARY EMBODIMENTS

Provided herein is a method for sample analysis. In some embodiments, the method may comprise: (a) incubating a sample comprising a target analyte with: (i) a first conjugate comprising a binding agent and first splint oligonucleotide, and (ii) a second conjugate comprising a binding agent and a second splint oligonucleotide, under conditions suitable for binding of the binding agents of the first and second conjugates to the target analyte, to produce a product, (b) incubating at least some of the product with: (i) a set of probes that produces a ligatable circle only when the probes are hybridized to the first and second splint oligonucleotides; and (ii) a ligase, to produce a reaction mix comprising covalently closed circular molecules, (c) treating at least some of the reaction mix with an exonuclease to terminate the ligation and degrade any nucleic acid that is not a covalently closed circular molecule; and, (d) after step (c), quantifying the amount of covalently closed circular molecules produced in the ligation step, i.e., the covalently closed circular molecules comprising the probes of step (b).

FIG. 1 schematically illustrates some of the components used in the present method. FIG. 1 shows: a first conjugate 2 comprising a binding agent 4 and first splint oligonucleotide 6, and (ii) a second conjugate 8 comprising a binding agent 10 and a second splint oligonucleotide 12. As shown, the first conjugate 2 and the second conjugate 8 are distinct molecules. As illustrated, probe set 14 comprises a first probe 16 and a second probe 18, the ends of which hybridize to the first splint oligonucleotide 6 and the second splint oligonucleotide 12 to produce a ligatable circle 19 that contains two nicks, 20 and 22. In this complex, the 5' end of the first probe is ligatably adjacent to the 3' end of the second probe and the 3' end of the first probe is ligatably adjacent to the 5' end of the second probe. Nicks 20 and 22 can be sealed by a ligase, thereby producing a covalently circular molecule 24 that has ligation junctions 26 and 28. As shown, two ligation events are required for circularization. As noted above, ligatable circle 19 can only be produced when the probes 16 and 18 are hybridized to the first splint oligonucleotide 6 and the second splint oligonucleotide 12, meaning that a ligatable circle is not produced when it is hybridized to only one or neither of the splint oligonucleotides. Because the ligatable circle can only be produced when both of the splint oligonucleotides are physically proximal to one another, the ligatable circle should only form when a molecule of the first conjugate 2 and a molecule of the second conjugate 8 bind to the same target analyte molecule. Some of the principles of other proximity ligation assays are described in Fredriksson (Nat. Biotechnol. 2002 20: 473-7) and Gullberg (Proc. Natl. Acad. Sci. 2004 101: 8420-4).

In some embodiments, the binding agents of the first and second conjugates are capture agents. In these embodiments, the method for sample analysis may comprise: (a) incubating a sample comprising an target analyte with: (i) a first conjugate comprising a capture agent and a first splint oligonucleotide, and (ii) a second conjugate comprising a capture agent and a second splint oligonucleotide, under conditions suitable for binding of the capture agents of the first and second conjugates to the target analyte, to produce a product,(b) incubating at least some of the product of step (a) with: (i) a set of probes that produces a ligatable circle only when the probes are hybridized to the first and second splint oligonucleotides; and (ii) a ligase, to produce a reaction mix comprising covalently closed circular molecules,(c) treating at least some of the reaction mix of step (b) with an exonuclease to terminate the ligation and degrade any nucleic acid that is not a covalently closed circular molecule; and (d) after step (c), quantifying the amount of covalently closed circular molecules produced in step (b).

For example, in some embodiments, the proteins of the first and second conjugates may be polyclonal antibodies, e.g., affinity-selected polyclonal antibodies, i.e., antibodies that have been obtained from an animal that has been immunized with the target analyte, or portion thereof. In these embodiments, two portions of a single batch of polyclonal antibody may be linked to different splint oligonucleotides, as described below. In other embodiments, the binding agents of the first and second conjugates may be matched monoclonal antibodies, where matched monoclonal antibodies bind to different sites in the antigen. Alternative non-antibody capture agents include, but are not limited to, aptamers and non-antibody proteins such as those described in Binz et al. (Curr Opin Biotechnol. 2005 16:459-69), Binz et al. (Nat. Biotechnol. 2005 23:1257-68), Forrer et al. (Chembiochem. 2004 5:183-9), Gronwall et al. (J. Biotechnol. 2009 140:254-69), Hosse et al. (Protein Sci. 2006 15:14-27) and Skerra et al. (Curr. Opin. Biotechnol. 2007 18:295-304), which are incorporated by reference herein.

In some embodiments, the binding agents of the first and second conjugates are not capture agents. In these embodiments, the target analyte may be an antibody (which, in its native form, contains two binding sites and, as such, can bind to two other molecules). In these embodiments, the method for sample analysis may comprise:(a) incubating a sample comprising an antibody with: (i) a first conjugate comprising a non-capture agent moiety, e.g., a protein, and a first splint oligonucleotide, and (ii) a second conjugate comprising a non-capture agent moiety, e.g., a protein and a second splint oligonucleotide, under conditions suitable for binding of the non-capture agent moieties of the first and second conjugates to the antibody, to produce a product,(b) incubating at least some of the product of step (a) with: (i) a set of probes that produces a ligatable circle only when the probes are hybridized to the first and second splint oligonucleotides; and (ii) a ligase, to produce a reaction mix comprising covalently closed circular molecules;(c) treating at least some of the reaction mix of step (b) with an exonuclease to terminate the ligation and degrade any nucleic acid that is not a covalently closed circular molecule; and (d) after step (c), quantifying the amount of covalently closed circular molecules produced in step (b). In these embodiments, two portions of a single batch of an isolated non-capture agent moiety, e.g., a protein, may be linked to different splint oligonucleotides, and used in the method.

In some embodiments, the binding agent may have a low affinity for the target analyte and some embodiments may have a $K_D$ in the range of $10^{-5}$ M to $10^{-9}$ M, $10^{-5}$ M to $10^{-8}$ M or $10^{-5}$ M to $10^{-7}$ M. In these embodiments, the binding agent may be a polyclonal antibody.

If the binding agent in a conjugate is an antibody, the antibody may be a "natural" antibody in which the heavy and light chains have been naturally selected by the immune system of a multi-cellular organism. Such antibodies have a stereotypical "Y"-shaped molecule that consists of four polypeptide chains; two identical heavy chains and two identical light chains connected by disulfide bonds. In other cases, an antibody may be an antibody fragment, a single chain antibody, or a phage display antibody, for example. An antibody may be a monoclonal antibody or a polyclonal antibody. If the antibodies used in the method are monoclonal, the antibodies bind to different epitopes. If polyclonal antibodies are used, an animal may be immunized with a single analyte (e.g., a protein) or portion thereof and a polyclonal population of antibodies may be affinity purified from the animal using the analyte or portion thereof. The affinity purified antibodies can be split and a first portion of the antibody population can be conjugated to the first splint oligonucleotide and a second portion of the antibody population can be conjugated to the second splint oligonucleotide.

If the binding agent in a conjugate is a non-capture agent polypeptide, the polypeptide may be prepared, a first portion (e.g., an aliquot) of the polypeptide may be linked to the first splint oligonucleotide, a second portion (e.g., an aliquot) of the polypeptide may be linked to the second splint oligonucleotide, and the products may be used to quantify the amount of an antibody that binds to the protein. Antibodies, in their natural form, contain two binding sites and, as such, the method can be readily implemented using a single polypeptide.

In a conjugate, the binding agent and splint oligonucleotide may be linked non-covalently (e.g., via a streptavidin/biotin interaction) or covalently (e.g., via a cycloaddition reaction or alternative chemistry). The splint oligonucleotide and the binding agent can be linked together via a number of different methods, including those that use a maleimide or halogen-containing group, which are cysteine-reactive. Oligonucleotides may be linked to agents, e.g., antibodies, using any convenient method (see, e.g., Gong et al., Bioconjugate Chem. 2016 27: 217-225 and Kazane et al., Proc Natl Acad Sci 2012 109: 3731-3736). A variety of linkage methods are available. For example, the splint oligonucleotides may be linked to the capture agents directly using any suitable chemical moiety on the capture agent (e.g., a cysteine residue or via an engineered site). In other embodiments, the splint oligonucleotides may be linked to the capture agents directly or indirectly via a non-covalent interaction, e.g., via a biotin/streptavidin or an equivalent thereof, via an aptamer or secondary antibody, or via a protein-protein interaction such as a leucine-zipper tag interaction or the like. The binding agent and the oligonucleotide may be linked at a site that is proximal to or at the 5' end of the oligonucleotide, proximal to or at the 3' end of the oligonucleotide, or anywhere in-between.

In some embodiments, each end of the probes is perfectly complementary to at least 6 contiguous nucleotides (e.g., 6 to 50 or 8 to 30 contiguous nucleotides, e.g., 6, 7, 8 or more nucleotides) of the splint oligonucleotides, although the method is expected to work if there are a few mismatches that do not significantly interfere with hybridization or ligation. In some embodiments, the oligonucleotides may be linked to the agents by a linker that spaces the oligonucleotide from the agents, if needed.

In some embodiments, the initial steps of the method may comprise combining a volume of a liquid sample with the conjugates in a suitable binding buffer, incubating the mix for a period of time, and then adding the probes and ligase to the mix. This initial step may be done by adding a relatively small volume of sample (e.g., 1-5 uL) directly to larger volume of the first and second conjugates in a binding buffer (e.g., 10 uL to 50 uL of buffer). In these embodiments, the sample may be diluted by at least 2x, at least 3x, at least 4x, at least 5x, or at least 10x. In the ligation step, the ligase used can be a ligase that has a substrate preference for sealing nicks in double-stranded DNA molecules, rather than for ligating single stranded DNA molecules together, thereby lowering background ligations. After the covalently closed circular molecules have been produced, the method may comprise treating at least some of the reaction mix with an exonuclease to terminate the ligation and degrade any nucleic acid that is not a covalently closed circular molecule. In some cases, the exonuclease may comprise both exonuclease I and exonuclease III, although other one or more other exonucleases, e.g., exonuclease T, exonuclease V, exonuclease VII, T5 exonuclease or T7 exonuclease could be used instead in some cases. In some embodiments, the exonuclease treatment step may be implemented by directly adding the one or more exonucleases to the ligation. The exonuclease treatment step should terminate the ligation and degrade any nucleic acid that is not a covalently closed circular molecule. This step cannot be incorporated into other methods in which the binding agents are linked to oligonucleotides that are used primers because, as would be apparent, the exonuclease would destroy the primers. In the present method, the first and second splint oligonucleotides are solely used as splints for ligating the probes together. The method does not comprise using the splint oligonucleotides as primers to amplify the covalently closed circular molecules. After exonuclease treatment, the exonucleases can be inactivated by any convenient method. In some embodiments, the exonucleases can be inactivated by heat treatment, e.g., by heating the reaction to a temperature of at least 60° C. for an extended period of time, e.g., at least 10 minutes. The conditions used for inactivating the exonuclease may depend on the exonucleases used.

After the covalently closed circular molecules are made, the method comprises quantifying the amount of covalently closed circular molecules. This may be done by a variety of different ways, with or without a preamplification step, e.g., by quantitative PCR or endpoint PCR (e.g., digital PCR, which can be implemented on plates or in droplets), using microarrays, or by sequencing. In sequencing embodiment, one or more of the probes may be indexed, which allows the molecules to be counted after sequencing.

In some embodiments, the covalently closed circular molecules may be quantified by quantitative PCR (qPCR), which assay may employ a double-stranded DNA-specific dye or a hydrolysis probe (e.g., a TaqMan assay or the like). Such quantitative PCR assays typically use a first primer that hybridizes to the covalently closed circular molecule and a second primer that hybridizes to the complement of the covalently closed circular molecule, thereby allowing part of the sequence of the covalently closed circular molecule to be amplified by PCR. In some embodiments, the first and second primers used for quantitative PCR may target the ligation junctions in the covalently closed circular molecules, thereby making the qPCR more specific. In these embodiments, the first primer hybridizes to a sequence that encompasses one of the ligation junctions, and the second primer hybridizes to the complement of a sequence that encompasses the other of the ligation junctions. In these embodiments, the 3' end of the first and second primers may extend one, two, three or, in some cases, four or more nucleotides past the ligation junction. In some embodiments, no pre-amplification of the covalently closed circular molecule is required prior to performing qPCR. Such pre-amplification methods typically used primers that bind to sites that are outside of the sites bound by the qPCR primers (such that the pre-amplification primers and the qPCR primers have a nested relationship). As such, the qPCR may be done without a pre-amplification step. Alternatively, the covalently closed circular molecules may be quantified by amplifying the covalently closed circular molecules by rolling circle amplification (RCA) to produce RCA products, and counting the RCA products. Such methods may be adapted from Larsson et al. (Nature Methods 2004 1: 227-232) among others. Several other methods for quantifying circular nucleic acid molecules are known or would be apparent to one of ordinary skill in the art.

In some embodiments, the initial steps of the method (up until the quantification step) can be implemented in a "single tube" format, in which reagent (e.g., enzyme, probes, etc.) are added directly to the prior reaction (after the reaction has been completed). In these embodiments, the binding, probe hybridization/ligation and exonuclease reactions (i.e., steps (a)-(c)) may be done in the same vessel. Specifically, the probe hybridization/ligation step (step (b)) may comprise adding reagents (the probes and ligase) to the vessel comprising the product of the binding step (step (a)), and the exonuclease treatment (step (c)) may comprises adding reagents (one or more exonucleases) to the vessel comprising the ligation product (of step (b)).

The method can be multiplexed using different sets of first and second conjugates for each target analyte. In these embodiments, the splint oligonucleotides of the conjugates that bind to a first analyte as well as the probes that hybridize to those splint oligonucleotides may be different from the splint oligonucleotides of the conjugates that bind to a second analyte as well as the probes that hybridize to those splint oligonucleotides. Since the different probe sets have different sequences, they can be assayed independently from one another by qPCR. As such, in some embodiments the sample may comprise a plurality of analytes, step (a) of the method may comprise incubating the sample with multiple pairs of said first and second conjugates, wherein each pair of conjugates binds to a different analyte; and step (d) comprises quantifying the number of covalently closed circular molecules corresponding to each analyte. In some embodiments, the analytes may be quantified in the same reaction, e.g., using multiplex qPCR. In other embodiments, the analytes may be quantified in different assays. In some embodiments, the analytes may be quantified in different assays, where each assay is, itself, a multiplex assay that contains an internal control (which can be used to, e.g., normalize the amount of the target analyte across samples). At least 2, at least 5 or at least 10 or more analytes may be quantified in a multiplexed manner using the present method.

The target analyte detected by the method may be any type of biological molecule to which antibodies can bind to different sites. Proteins are one type of target analyte. In some embodiments, both conjugates may bind to a single protein. In other embodiments, the analyte may be a complex of proteins. In these embodiments, the first and second binding agents may bind to different proteins in the complex.

In some embodiments, sample is a bodily fluid or a processed form thereof. Bodily fluids of interest include plasma, saliva and urine, although several other bodily fluids may be used in the present method. Bodily fluids include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, and urine. In some embodiments, a sample may be obtained from a subject, e.g., a human, and it may be processed prior to use in the subject assay. For example, prior to analysis, the protein may be extracted from a tissue sample prior to initiating the present method. In particular embodiments, the sample may be a clinical sample, e.g., a sample collected from a patient.

The present method may have a sensitivity of at least 5 fM, 10 fM, 50 fM, 100 fM, 0.5 pM, 1 pM, 5 pM, 10 pM, 50 pM, 100 pM, 0.5 nM, 1 nM, 5 nM, 10 nM, 50 nM or 100 nM depending on the target analyte.

Without wishing to be bound to any particular use, the present method has particular utility in analyzing blood plasma. Blood plasma can be obtained non-invasively and it contains a variety of different, low abundance proteins that are diagnostic, prognostic or theranostic (see, generally, Anderson et al., Molecular & Cellular Proteomics 2002 1: 845-867 and Anderson et al., Clinical Chemistry 2010 56: 177-185). As such, in some embodiments, the present method may be used to quantify any one or combination (e.g., 2, 3, 4, 5 or more) of the following proteins in plasma: acid phosphatase, IgG, alanine aminotransferase (ALT or SGPT), IgM, albumin, inhibin-A, aldolase, insulin, alkaline phosphatase (ALP), insulinlike growth factor-I (IGF-I), α-1-acid glycoprotein (orosomucoid), insulinlike growth factor-II (IGF-II), α-1-antitrypsin, IGFBP-1, α-2-antiplasmin, IGFBP-3, α-2-HS-glycoprotein, interleukin-2 receptor (IL-2R), α-2-macroglobulin, isocitric dehydrogenase, α-fetoprotein (tumor marker), K light chains, amylase, lactate dehydrogenase heart fraction (LDH-1), amylase, lactate dehydrogenase liver fraction (LLDH), ACE, lactoferrin, antithrombin III (ATIII), A light chains, apolipoprotein A1, lipase, apolipoprotein B, Lp(a), aspartate aminotransferase (AST or SGOT), lipoprotein-associated phospholipase A2 (LP-PLA2), 3-2 microglobulin, LH, 3-thromboglobulin, lysozyme, biotinidase, macrophage migration inhibitory factor (MIF) myeloperoxidase (MPO), cancer antigen 125 (CA 125), myoglobin, cancer antigen 15-3 (CA 15-3), osteocalcin, cancer antigen, human epididymis protein (HE4), parathyroid hormone, carcinoembryonic antigen (CEA), phosphohexose isomerase, ceruloplasmin, plasminogen, cholinesterase, plasminogen activator inhibitor (PAI), complement C1, prealbumin, complement C1 Inhibitor, NTproBNP, complement C1Q, procalcitonin (PCT), complement C3, prolactin, complement C4, properdin factor B, complement C5, prostatic acid phosphatase (PAP), CRP, prostatic specific antigen (PSA), creatine kinase-BB (CKBB), protein C, creatine kinase-MM (CKMM), protein S, cystatin C, pseudocholinesterase, erythropoietin, pyruvate kinase, factor IX antigen, renin, factor X, retinol binding protein (RBP), factor XIII, sex hormone-binding globulin, ferritin, soluble mesothelin-related peptide, fibrinogen, sorbital dehydrogenase (SDH), fibronectin, thyroglobulin, FSH, TSH, GGT, thyroxine binding globulin (TBG), haptoglobin, tissue plasminogen activator (T-PA), human chorionic gonadotropin (hCG), transferrin, hemopexin, transferrin receptor (TFR), her-2/neu protein, troponin T (TnT), human growth hormone (HGH), TnI (cardiac), human placental lactogen (HPL), trypsin, IgA, urokinase, IgD, Von Willebrand factor, IgE, nucleotidase, IgG subclass 4, ADAMTS13 activity and inhibitor, inhibin B (infertility), adenosine deaminase, IGFBP-2, adiponectin, intercellular adhesion molecule 1, a subunit of pituitary glycoprotein hormones, interferon-γ, α-galactosidase, interferon-α, EIA, α-N-acetylglucosaminidase, interleukin-1 receptor antagonist, amyloid 13-protein, interleukin-1 soluble receptor type II, angiotensinogen, interleukin-1α, anti-Mullerian hormone (AMH), interleukin-113, 3-glucuronidase, interleukin-2, 3-N-acetylglucosaminidase, interleukin-3, calprotectin, interleukin-4, cancer antigen 72-4, interleukin-5 cholecystokinin, interleukin-6, complement C2, interleukin-7, complement C4 binding protein, interleukin-8, complement C6, interleukin-9, complement C7 level, interleukin-10, complement C8 level, interleukin-11, complement C9 level, interleukin-12, corticosteroid binding globulin (transcortin), interleukin-13, CYFRA 21-1 (soluble cytokeratin fragment), interleukin-14, dopa decarboxylase, interleukin-15, elastase, interleukin-16, eosinophil cationic protein, interleukin-17, epidermal growth factor, interleukin-18, epidermal growth factor receptor (EGFR), kallikrein, factor II, leptin, factor V, leucine aminopeptidase, factor VII, mannose-binding lectin, factor VIII, neuron-specific enolase (NSE), factor XI, neurophysin, factor XII, pancreastatin, fibroblast growth factor (FGF2), pepsinogen I, gastric inhibitory polypeptide (GIP), pepsinogen II, Glial cell-derived neurotrophic factor (GDNF), glutathione peroxidase, proteasome activity, plasma-based Leumeta, granulocyte colony-stimulating factor, S-100B protein, granulocyte-macrophage colony-stimulating factor, soluble CD30, growth hormone binding protein, squamous cell carcinoma antigen, hemoglobin, thyrotropin releasing hormone (TRH), heparin cofactor II, transforming growth factor-131, hexosaminidase A and total hexosaminidase, tumor necrosis factor receptor 1, high molecular weight kininogen, tumor necrosis factor receptor 2, human growth hormone-releasing hormone (HGH-RH), tumor necrosis factor-α, IgG subclass 1, tumor necrosis factor-13, IgG subclass 2, vascular endothelial growth factor (VEGF), IgG subclass 3, and vitamin D-binding protein.

As would be apparent, the method may also be employed to identify a microbial (e.g., bacterial or viral) pathogen in a clinical sample, e.g., a cell surface protein or secreted protein. In these embodiments, the capture agents may target proteins or other moieties from a pathogen. If circles are detected, then the subject may be diagnosed as being infected by that pathogen. Microbes that might be identified using the present methods, compositions and kits include but are not limited to: viruses, yeast, Gram (+) bacteria, Gram (−) bacteria, bacteria in the family Enterobacteriaceae, bacteria in the genus *Enterococcus*, bacteria in the genus *Staphylococcus*, and bacteria in the genus *Campylobacter*, *Escherichia coli* (*E. coli*), *E. coli* of various strains such as, K12-MG1655, CFT073, O157:H7 EDL933, O157:H7 VT2-Sakai, etc., *Streptococcus pneumoniae, Pseudomonas aeruginosa, Staphylococcus aureus*, coagulase-negative staphylococci, a plurality of *Candida* species including *C. albicans, C. tropicalis, C. dubliniensis, C. viswanathii, C. parapsilosis, Klebsiella pneumoniae*, a plurality of *Mycobacterium* species such as *M. tuberculosis, M. bovis, M. bovis* BCG, *M. scrofulaceum, M. kansasii, M. chelonae, M. gordonae, M. ulcerans, M. genavense, M. xenoi, M. simiae, M. fortuitum, M. malmoense, M. celatum, M. haemophilum* and *M. africanum, Listeria* species, *Chlamydia* species, *Mycoplasma* species, *Salmonella* species, *Brucella* species, *Yersinia* species, etc. Thus, the subject method enables identification of microbes to the level of the genus, species, sub-species, strain or variant of the microbe.

In some embodiments, the results of the method may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective). In some embodiments, the method may be used to analyze a group of 1, 2, 3, 4, 5, 6, 7, 8, 9 or 10 or more analytes that are independently either present at a higher concentration or lower concentration relative to a control (e.g., an internal control), where collectively the identity of the analytes and their abundance correlate with a phenotype.

The method may be used to analyze a patient sample. In this embodiment, the method may comprise: (a) quantifying, using the above-described method, one or more analytes in a sample and (b) providing a report indicating a correlation with phenotype. This embodiment may further comprise making a diagnosis, prognosis or theranosis based on the report. The report may indicate the normal range of the analyte.

In some embodiments, the method may involve creating a report as described above (an electronic form of which may have been forwarded from a remote location) and forwarding the report to a doctor or other medical professional to determine whether a patient has a phenotype (e.g., cancer, etc.) or to identify a suitable therapy for the patient. The report may be used as a diagnostic to determine whether the subject has a disease or condition, e.g., a cancer. In certain embodiments, the method may be used to determine the stage or type of cancer, to identify metastasized cells, or to monitor a patient's response to a treatment, for example.

In any embodiment, report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information refers to transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or email transmissions and information recorded on websites and the like. In certain embodiments, the report may be analyzed by an MD or other qualified medical professional, and a report based on the results of the analysis of the image may be forwarded to the patient from which the sample was obtained.

Kits

Also provided by this disclosure are kits that contain reagents for practicing the subject methods, as described above. The subject kits contain one or more of any of the components described above. In some embodiments a kit may comprise: (i) a first splint oligonucleotide, (ii) a second splint oligonucleotide, (iii) a set of probes that produces a ligatable circle only when the probes are hybridized to the first and second splint oligonucleotides, and (iv) one or more exonucleases. In these embodiments, the splint oligonucleotides may have reactive ends that can react with/bind to a binding agent, as discussed above. In some embodiments, the kit may also contain a binding agent and, in some embodiments, the splint oligonucleotides are conjugated to the binding agent in the kit. In some embodiments, a kit may further comprise a ligase and/or primers for performing quantitative PCR analysis, as described above. In some embodiments, the primers target the ligation junctions in the ligatable circles produced by hybridizing the splint oligonucleotides to the probes. In these embodiments, one primer may hybridize to a sequence that encompasses one of the ligation junctions, and the other primer hybridizes to the complement of a sequence that encompasses the other of the ligation junctions.

The various components of the kit may be present in separate containers or certain compatible components may be precombined into a single container, as desired.

In addition to the above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, the means for obtaining the instructions is recorded on a suitable substrate.

EMBODIMENTS

Embodiment 1. A method for sample analysis comprising:
(a) incubating a sample comprising a target analyte with:
(i) a first conjugate comprising a binding agent and a first splint oligonucleotide, and
(ii) a second conjugate comprising a binding agent and a second splint oligonucleotide,
under conditions suitable for binding of the binding agents of the first and second conjugates to the target analyte, to produce a product;
(b) incubating at least some of the product of step (a) with:
(i) a set of probes that produces a ligatable circle only when the probes are hybridized to the first and second splint oligonucleotides; and
(ii) a ligase;
to produce a reaction mix comprising covalently closed circular molecules;
(c) treating at least some of the reaction mix of step (b) with an exonuclease to terminate the ligation and degrade any nucleic acid that is not a covalently closed circular molecule; and
(d) after step (c), quantifying the amount of covalently closed circular molecules produced in step (b).

Embodiment 2. The method of embodiment 1, wherein the binding agents of the first and second conjugates are capture agents.

Embodiment 3. The method of any prior embodiment, e.g., embodiment 1, wherein the binding agents of the first and second conjugates are affinity-selected polyclonal antibodies.

Embodiment 4. The method of any prior embodiment, e.g., embodiment 1, wherein the binding agents of the first and second conjugates are matched monoclonal antibodies.

Embodiment 5. The method of embodiment 1, wherein the binding agent of the first and second conjugates are not capture agents.

Embodiment 6. The method of any prior embodiment, wherein the first and second conjugates bind to the target analyte with a low affinity.

Embodiment 7. The method of any prior embodiment, wherein the quantifying step (d) is done by quantitative PCR, digital PCR, by hybridization to a microarray or by sequencing.

Embodiment 8. The method of embodiment 7, wherein the primers used for the quantitative PCR target the ligation junctions in the covalently closed circular molecules of (d).

Embodiment 9. The method of any prior embodiment, e.g., any of embodiments 1-2, wherein step (d) comprises amplifying the covalently closed circular molecules by rolling circle amplification (RCA) to produce RCA products.

Embodiment 10. The method of embodiment 9, wherein the method comprises counting the RCA products.

Embodiment 11. The method of any prior embodiment, wherein the reactions of steps (a)-(c) are done in the same vessel.

Embodiment 12. The method of embodiment 11, wherein step (b) comprises adding the set of probes and ligase to the vessel comprising the product of step (a), and step (c) comprises adding one or more exonucleases to the vessel comprising the ligation product of step (b).

Embodiment 13. The method of any of prior embodiment, wherein:

(i) the sample comprises a plurality of target analytes,
(ii) step (a) comprises incubating the sample with multiple pairs of said first and second conjugates, wherein each pair of conjugates binds to a different target analyte; and
(iii) step (d) comprises quantifying the number of covalently closed circular molecules corresponding to each target analyte.

Embodiment 14. The method of any prior embodiment, wherein the sample is from a bodily fluid.

Embodiment 15. The method of embodiment 11, wherein the bodily fluid is blood plasma, saliva or urine.

Embodiment 16. The method of any prior embodiment, wherein the target analyte is a protein.

Embodiment 17. A kit comprising:
(i) a first splint oligonucleotide, and
(ii) a second splint oligonucleotide;
(iii) a set of probes that produces a ligatable circle only when the probes are hybridized to the first and second splint oligonucleotides;
(iv) one or more exonucleases.

Embodiment 18. The kit of embodiment 17, further comprising a ligase.

Embodiment 19. The kit of embodiment 17 or 18, further comprising a binding agent to which the first and second splint oligonucleotides can be conjugated.

Embodiment 20. The kit of any of embodiments 17-19, further comprising primers for performing quantitative PCR (qPCR) analysis.

EXAMPLES

Aspects of the present teachings can be further understood in light of the following examples, which should not be construed as limiting the scope of the present teachings in any way.

Presented herein is a highly specific protein detection method, referred to as the circular proximity ligation assay (c-PLA), that outperforms traditional PLA in stringency, ease of use, reproducibility and compatibility with low affinity reagents. In c-PLA, two proximity-probes bind to an analyte providing a scaffolding that positions two free oligonucleotides such that they can be ligated into a circular DNA molecule. This assay format stabilizes antigen proximity-probe complexes and enhances stringency by reducing the probability of random background ligation events. Circle formation also increases selectivity since the uncircularized DNA can be removed enzymatically. This method has been compared to traditional PLA on several biomarkers and demonstrate that the higher stringency for c-PLA improves reproducibility and enhances sensitivity in both buffer and human plasma. The limit-of-detection ranges from femtomolar to nanomolar concentrations for both methods. Kinetic analysis using surface plasmon resonance (SPR) and biolayer interferometry (BLI) reveal that the variation in limit-of-detection is due to the variation in antibody affinity, and that c-PLA outperforms traditional PLA for low affinity antibodies. The lower background signal can be used to increase proximity-probe concentration while maintaining a high signal-to-noise ratio, thereby enabling the use of low affinity reagents in a homogeneous assay format. It is anticipated that the advantages of c-PLA will be useful in a variety of clinical protein detection applications where high affinity reagents are lacking.

c-PLA a highly specific, sensitive, and convenient assay for quantitative protein detection. The method builds on the existing PLA, but also benefits from the formation of circular DNA molecules. Proximity ligation assays combined with circle formation have traditionally been used for rolling circle amplification and have shown impressive results for in-situ detection and digital quantification. It has been demonstrated that the circle formation increases reproducibility by minimizing noise across the linear dynamic range. This is facilitated by the inclusion of exonuclease treatment, which hydrolyzes non-circular DNA. This design also simplifies the workflow as it eliminates the need for preamplification prior to qPCR quantification without any loss in assay performance. Both methods were compared using six commonly used biomarkers and demonstrate equal or better performance for circular PLA.

The kinetic analysis of the required antibody-antigen interactions, an essential precaution rarely taken during assay development for protein detection, demonstrates a direct correlation between kinetic constants and assay performance. The value of kinetic information to screen for suitable antibodies prior to proximity-probe conjugation and to optimize proximity-probe concentrations as well as assay procedures has established. This work thus indicates that the regular use of kinetic analysis will be highly beneficial in improving assay performance across a wide variety of analytes.

The advantages of c-PLA over t-PLA for low affinity interactions are aided by suppressed dissociation provided by longer DNA duplexes. It has been shown that the additional proofreading step facilitated by the extra oligo in circular PLA can be exploited to increase proximity-probe concentration without a concomitant increase in background ligation. This improves the signal-to-noise ratio and limit-of-detection compared to t-PLA and enables the use of low affinity reagents. This is a major benefit as low-affinity antibodies and variation in antibody specificity often contribute to systematic errors in research and clinical diagnostics (51). It has been also demonstrated that the benefits of c-PLA over t-PLA persist in complex media such as human plasma. This will facilitate new applications when high affinity reagents are not available, allowing not only new analytes to be detected, but also greater sensitivity for protein detection. These advantages are strengthened by the ease of application of the assay as well as its amenability to automation and a variety of quantification methods (digital, fluorescent, electrical, and more). The formation of circular DNA also supports detection using rolling circle amplification and other isothermal amplification methods that can be accomplished on low-cost point-of-care devices (52, 53). It is anticipated that an assay of this versatility and performance will help pave the way for much broader adoption of protein quantification into clinical and even resource-poor settings.

Results

Figure 2:
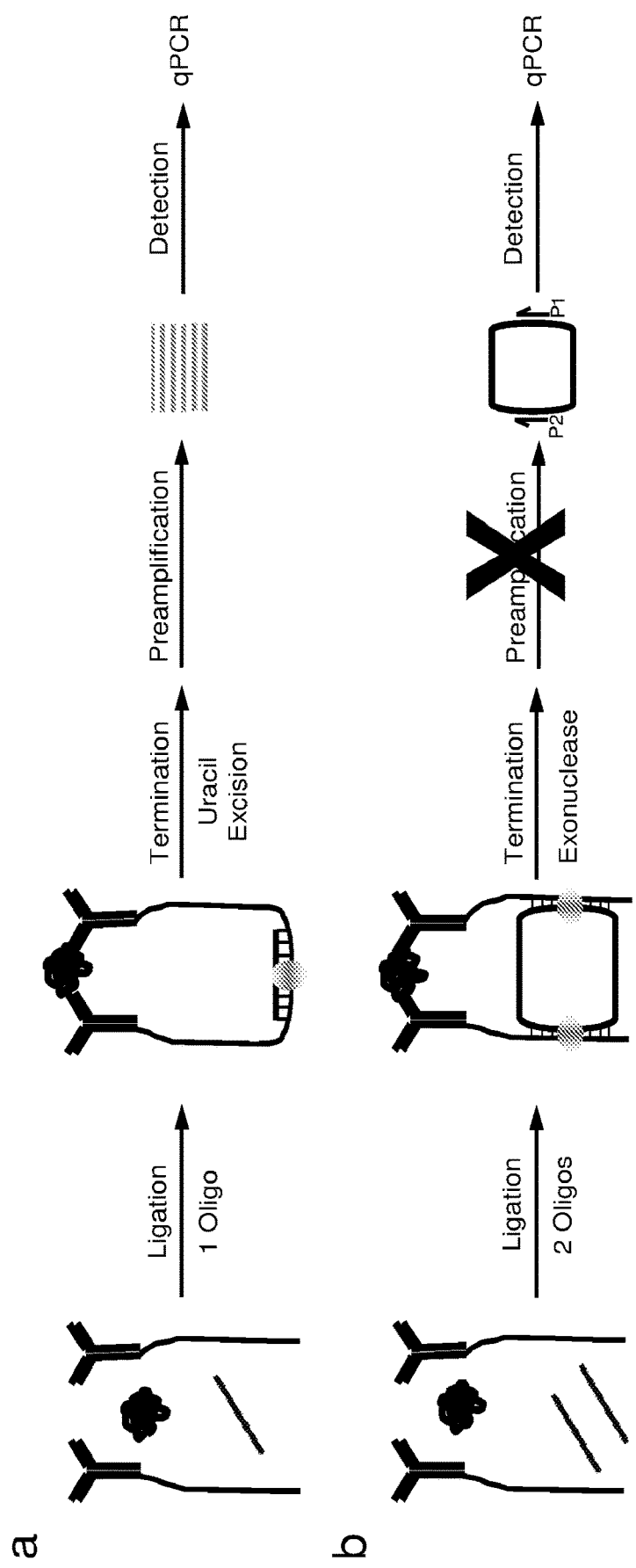
FIG. 2. Schematic representation of traditional and circular proximity ligation assay. a) Traditional proximity ligation assay (t-PLA) detects proteins using pairs of antibody-DNA conjugates (red and blue) which are brought into close proximity upon binding to target analyte. The addition of a bridge oligonucleotide and DNA ligase enables ligation of the antibody-tethered oligonucleotides to form a new DNA sequence. Ligation is terminated by selective degradation of the bridge oligonucleotide. The newly formed ligation product is subsequently preamplified followed by quantification using qPCR. b) In circular proximity ligation assay (c-PLA) the antibody-tethered oligonucleotides act as bridges for two ligation events between free oligonucleotides resulting in the formation of a circular ligation product. The addition of an extra oligonucleotide increases stringency compared to traditional PLA as it lowers the probability of random background ligation events since four components must assemble in the absence of the target analyte to generate an independent circular ligation product. Circle formation also allows exonuclease treatment, which terminates ligation and reduces background by degrading all uncircularized DNA. The reduction in background also simplifies the workflow by eliminating the need for preamplification. Circular ligation products are quantified by qPCR using primer sites spanning the newly formed junctions (P1 and P2).

Circular proximity ligation assay workflow. The workflows for both the traditional proximity ligation assay (t-PLA) and the circular proximity ligation assay (c-PLA) are shown in FIG. 2. Both assays utilize the same set of proximity-probes that are prepared by bioconjugation of polyclonal antibodies with amine-modified oligonucleotides through aromatic hydrazone chemistry (details provided in FIG. 7 and Materials and Methods). Polyclonal antibodies are cost-efficient, as a single batch of antibodies is divided into two portions and coupled to oligonucleotides that are terminated by either a phosphorylated 5'-end or a 3'-end, respectively. This produces two heterogeneous mixtures of proximity-probes against several different epitopes of the same target antigen. During sample incubation, the antibody portions of these proximity-probes bind to distinct epitopes of the target analyte. This is followed by a ligation step in which a solution containing DNA ligase is added to the incubation mixture. In t-PLA this ligation mixture contains a third bridge oligonucleotide complementary to the ends of the proximity-probes, thereby facilitating ligation to form a new DNA sequence. Ligation is terminated by the addition of a uracil-excision mixture, which selectively degrades the bridge oligonucleotide. The ligation mixture is subsequently preamplified across the newly formed DNA junction to increase signal-to-background ratio and reproducibility (12, 35) prior to quantification by qPCR. In c-PLA, ligation products are not formed by a direct junction of proximity-probes, but rather by the formation of a circle when two free connector oligonucleotides are joined in two distinct ligation events facilitated by target-bound proximity-probes. The uracil excision step is replaced with exonuclease treatment, which has the selective advantage of enriching for circularized DNA (32). Consequently, the background is dramatically decreased as all uncircularized nucleic acids are degraded, as opposed to only the bridge oligo in t-PLA. This allows for omission of the preamplification prior to qPCR analysis without any loss in signal-to-noise ratio or reproducibility.

Assay characteristics. c-PLA was designed from existing traditional PLA probes that have been optimized for minimization of heteroduplex formation (12). This allowed a comparison of the two methods using the same set of proximity-probes. For c-PLA, the ligation conditions were relaxed to account for the requirement of two ligation events and to accommodate the efficiency of Ampligase at higher temperature. Ligation was consequently performed for 30 min at 45° C. instead of 15 min at 30° C. A comparable modification of t-PLA did not yield any improvements.

Figure 3:
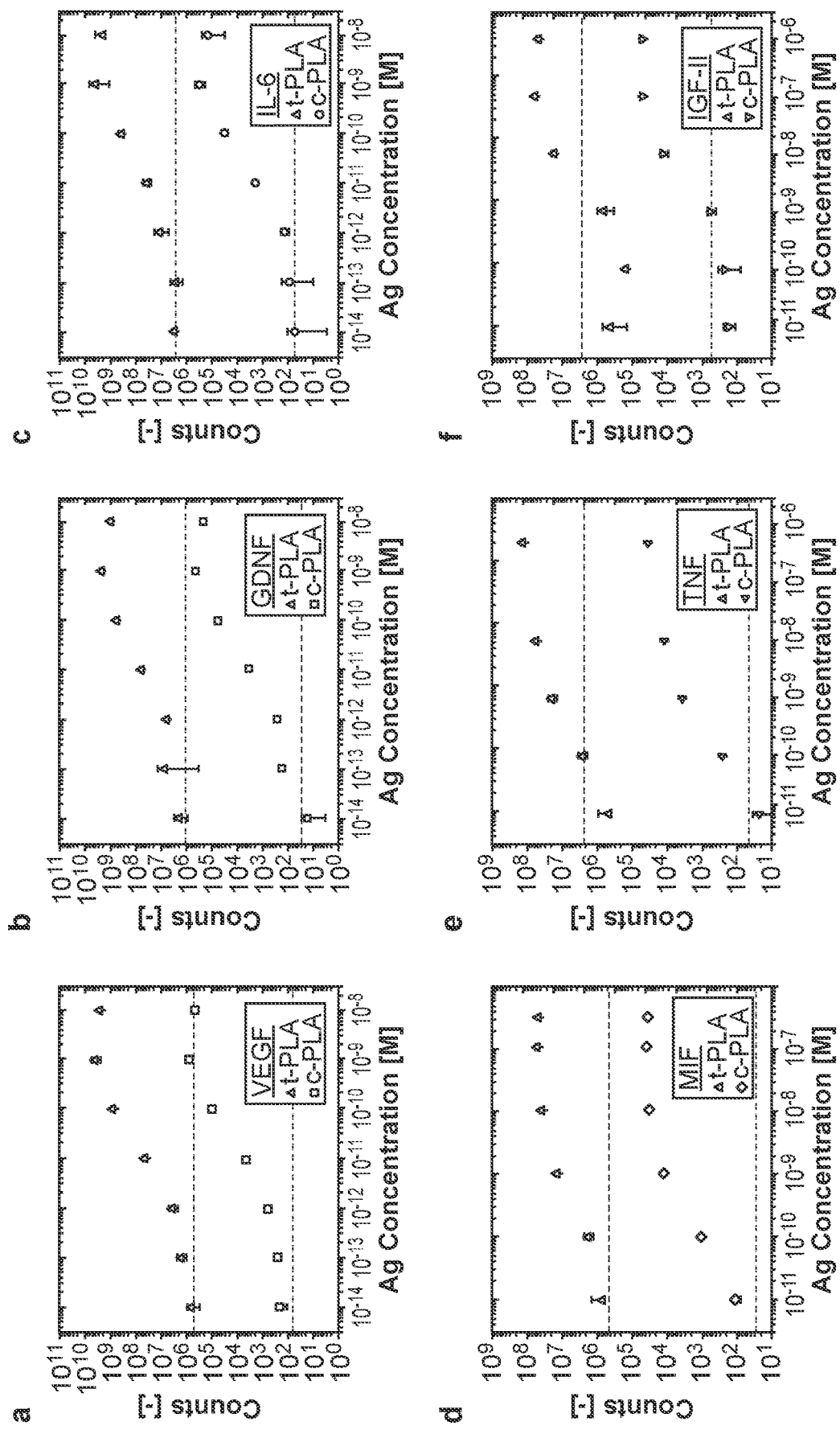
FIG. 3. Dose-response curves of traditional and circular PLA for detection of VEGF (a), GDNF (b), IL-6 (c), MIF (d), TNF-α (e), and IGF-II (f). The x-axis display& antigen concentration and the y-axis an estimated number of ligated molecules. The enhanced stringency for c-PLA is demonstrated by a lower number of counts because of the rigor imposed by circle formation, background reduction through exonuclease treatment, elimination of preamplification and tailored qPCR primer sites. Error bars denote one standard deviation (n=9) and the dashed lines denote limit-of-detection, defined as the mean signal of a blank sample+3 SD.
Figure 8:
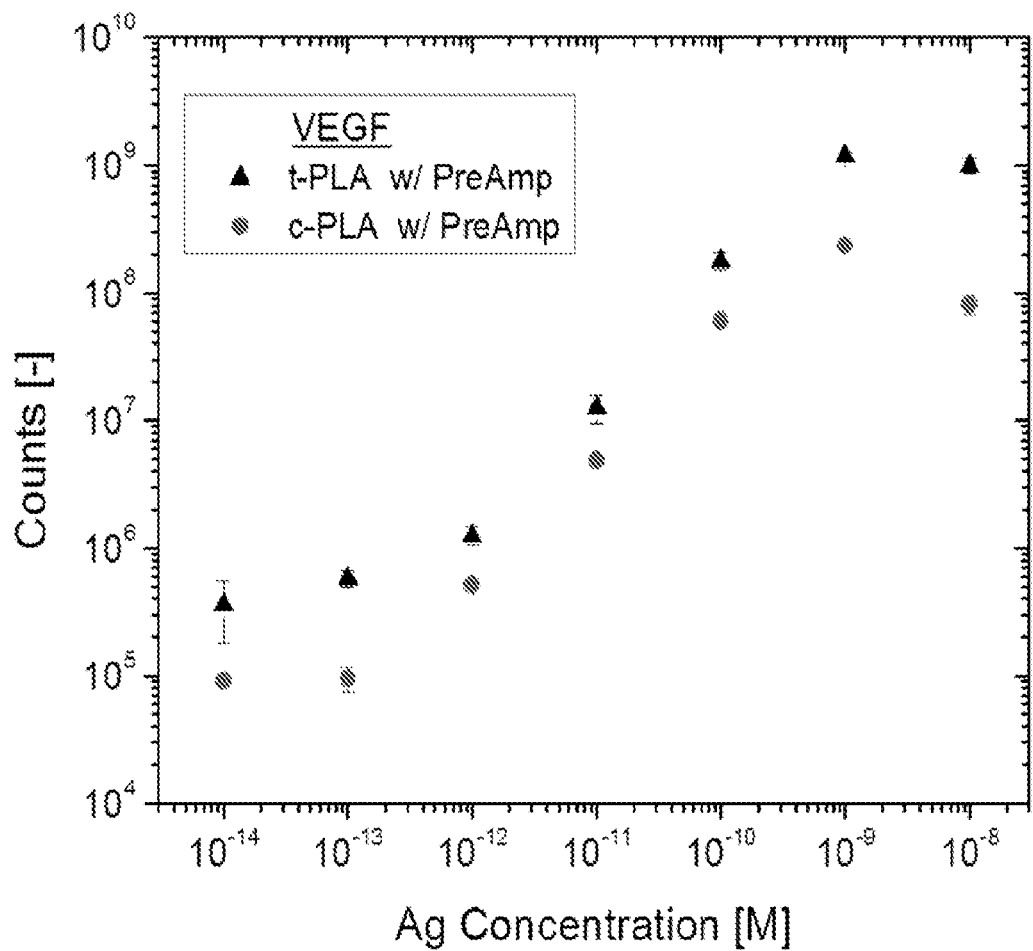
FIG. 8. Preamplification comparison between circular and traditional PLA for VEGF. The difference in counts (estimated number of ligated molecules) between preamplified c-PLA and t-PLA reflects the increased rigor in assay design for c-PLA.

A direct comparison between traditional and circular PLA for six biomarkers are shown in FIG. 3 and the results are summarized in Table 1. These experiments were performed with three biological replicates and quantified in triplicate qPCR experiments generating nine data points for each concentration. For vascular endothelial growth factor (VEGF), a dose-dependent response across nearly 5 orders of magnitude is demonstrated for both methods (FIG. 3*a*). The difference of almost 4 orders of magnitude in counts (estimated number of ligated molecules) generated by the two methods is due to both the elimination of preamplification as well as the enhanced stringency for c-PLA. For comparison, preamplification in c-PLA was performed and found that the omission of this step accounts for approximately 3 orders of magnitude difference in signal, whereas stringency in assay design accounts for the remainder (FIG. 8). Preamplification was originally introduced to improve signal-to-background ratio and precision although t-PLA is still impeded by relatively high CVs (coefficient of variation), an obstacle for standard use in clinical diagnostics. Variation in t-PLA has traditionally been addressed by addition of internal controls and normalization of data allowing for relative biomarker profiling (13, 15). Background signals for PLA are generated from random ligation events, non-specific binding of two cognate proximity-probes or nucleic acid amplification artifacts. In c-PLA, random ligation events are minimized by the stringency in assay design as four molecules and two ligation events are required for signal generation. Non-specific binding effects are addressed by the addition of excess bulk IgG molecules from the same species as the proximity-probes (12). Nucleic acid amplification artifacts are minimized in c-PLA as dual ligation events result in two new DNA sequences at the junction sites. Multiple primers targeting different sites on the newly formed circular DNA were tested and found that a primer pair spanning both junctions produced the lowest background. Exonuclease treatment in c-PLA also reduces background, which enhances signal-to-noise ratio and assay performance. This improves precision within the linear dynamic range as demonstrated by a decrease in the average CVs from 29% for t-PLA to below 16% for c-PLA (Table 1). PLA precision in general is limited by the qPCR readout and variation at low counts can be decreased further with digital quantification methods (31, 36).

TABLE 1

Comparison of limit-of-detection and dynamic range for six biomarkers measured by circular and traditional PLA.

| Analyte | Function | Data in Figure | Circular PLA (c-PLA) | | | Traditional PLA (t-PLA) | | |
|---|---|---|---|---|---|---|---|---|
| | | | Limit-Of-Detection | Dynamic Range | CVs | Limit-Of-Detection | Dynamic Range | CVs |
| VEGF | Growth Factor | 3a | <10 fM | <5 | 15.6% | 10 fM | <5 | 29.3% |
| GDNF | Cell Survival | 3b | 15 fM | <5 | 12.4% | 10 fM | 5 | 30.8% |
| IL-6 | Inflammation | 3c | 100 fM | <4 | 28.2% | 150 fM | <4 | 48.5% |
| MIF | Innate Immunity | 3d | 3 pM | 3 | 10.4% | 5 pM | 3 | 39.9% |
| TNF-α | Cell Signaling | 3e | 20 pM | 3 | 19.4% | 70 pM | <3 | 44.2% |
| IGF-II | Inflammation | 3f | 1 nM | 2 | 17.0% | 3 nM | <2 | 24.3% | c-PLA was compared to traditional PLA for five additional biomarkers, glial cell line derived neurotrophic factor (GDNF), interleukin 6 (IL-6), macrophage migration inhibitory factor (MIF), tumor necrosis factor alpha (TNF-α), and insulin-like growth factor II (IGF-II) (FIG. 3b-f, raw data provided in Tables 5-10.). It was found that the higher stringency for c-PLA yielded improvements in precision, signal-to-background ratios, and equal or better assay performance in terms of limit-of-detection and dynamic range for all analytes except GDNF. Average CVs across the linear range were all below 20% for c-PLA, with the exception of IL-6 (28%), while CVs for t-PLA varied from 24% to 48%. Reproducibility is generally better at higher concentrations, while precision deteriorates at low concentrations. This represents a common problem for PLA and other highly sensitive methods for protein quantitation (37-39).

A notable observation is that the limit-of-detection for the analytes varies more than 5 orders of magnitude from low femtomolar to nanomolar concentration and that the dynamic range is confined by the limit-of-detection on the lower end and the proximity-probe concentration on the upper end where the hook effect starts to interfere. Consequently IGF-II, which exhibits the worst limit-of-detection (1 nM) among the analytes that were tested, also displays a restricted dynamic range of about 2 orders of magnitude. The assay performance for the same biomarkers in t-PLA generally follows the same trend as found for c-PLA, albeit with a slightly higher limit-of-detection. It is noted that previous proximity ligation studies of the same analytes have reported limit-of-detection using various definitions (12, 15). Here the limit-of-detection is strictly defined as the mean signal corresponding to a blank sample plus three standard deviations (40). Discrepancies in reported limit-of-detection can be affected by the use of alternative definitions, differences in protocol, or by batch-to-batch variation in proximity-probe conjugation, as affinity probes without conjugated oligonucleotides may bind to target analytes and interfere with the ability to facilitate ligation. One benefit of using the same batch of proximity-probes for both traditional and circular proximity ligation is that such effects are eliminated, making comparison between the two methods more straightforward. Furthermore, keeping the oligonucleotide sequences constant for all analytes eliminates any variation that may arise from sequence specificity, albeit this limits the possibility of multiplexing for the purpose of this investigation. The similarities in performance between the two methods indicate that the variation in limit-of-detection between analytes is inherently an effect of the quality of the proximity-probes and their ability to enable antibody-antigen interactions.

Figure 4:
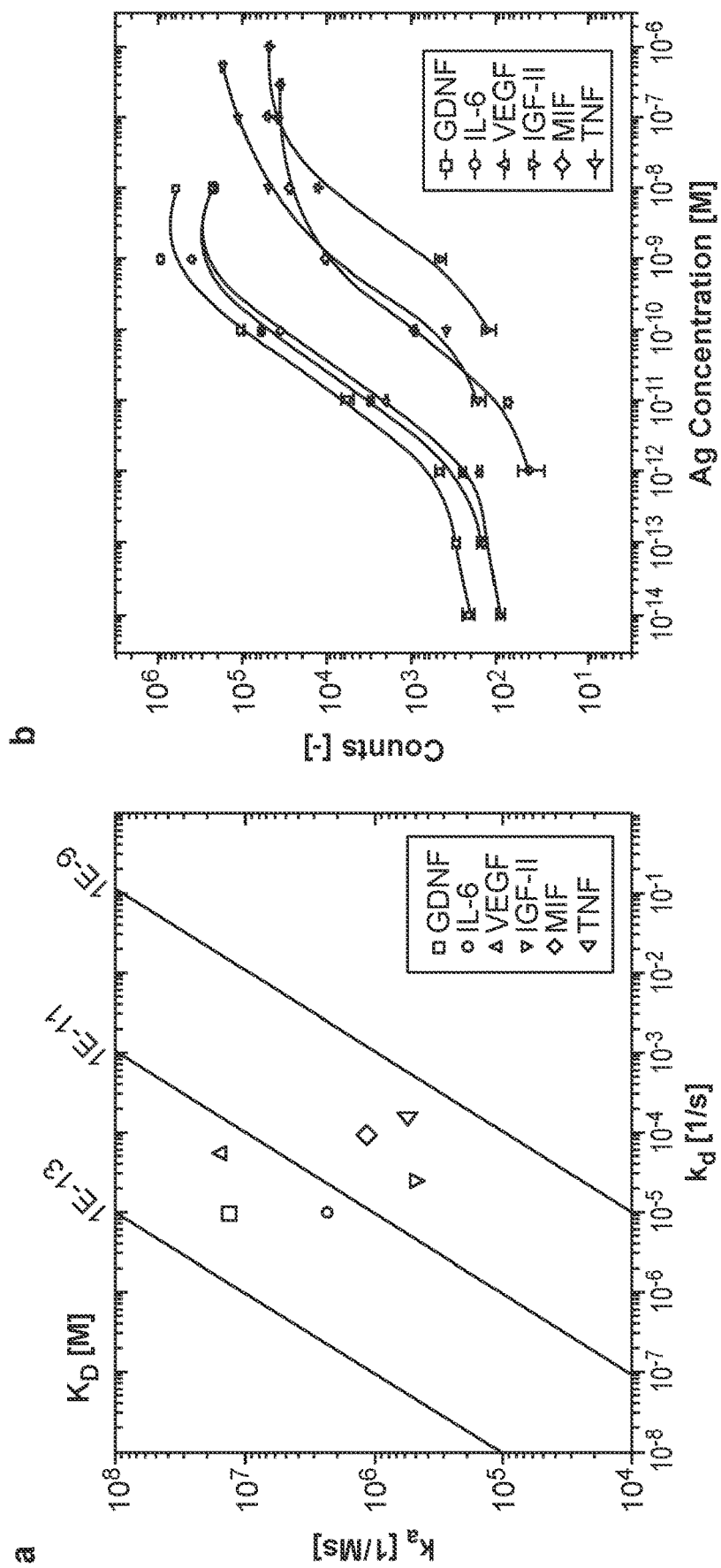
FIG. 4. Isoaffinity analysis and corresponding circular PLA performance for six biomarkers. a) Kinetic analysis reveals two distinct groups for $K_D$ values, one group with high affinity (single digit pM) and another group with affinity above 50 pM. b) The differences in antibody affinities are directly reflected in the c-PLA dose-response curves, where analytes with low $K_D$ values display limits-of-detection in the sub-pM range while the other group exhibits limits-of-detection in the mid-pM range or higher.
Figure 10:
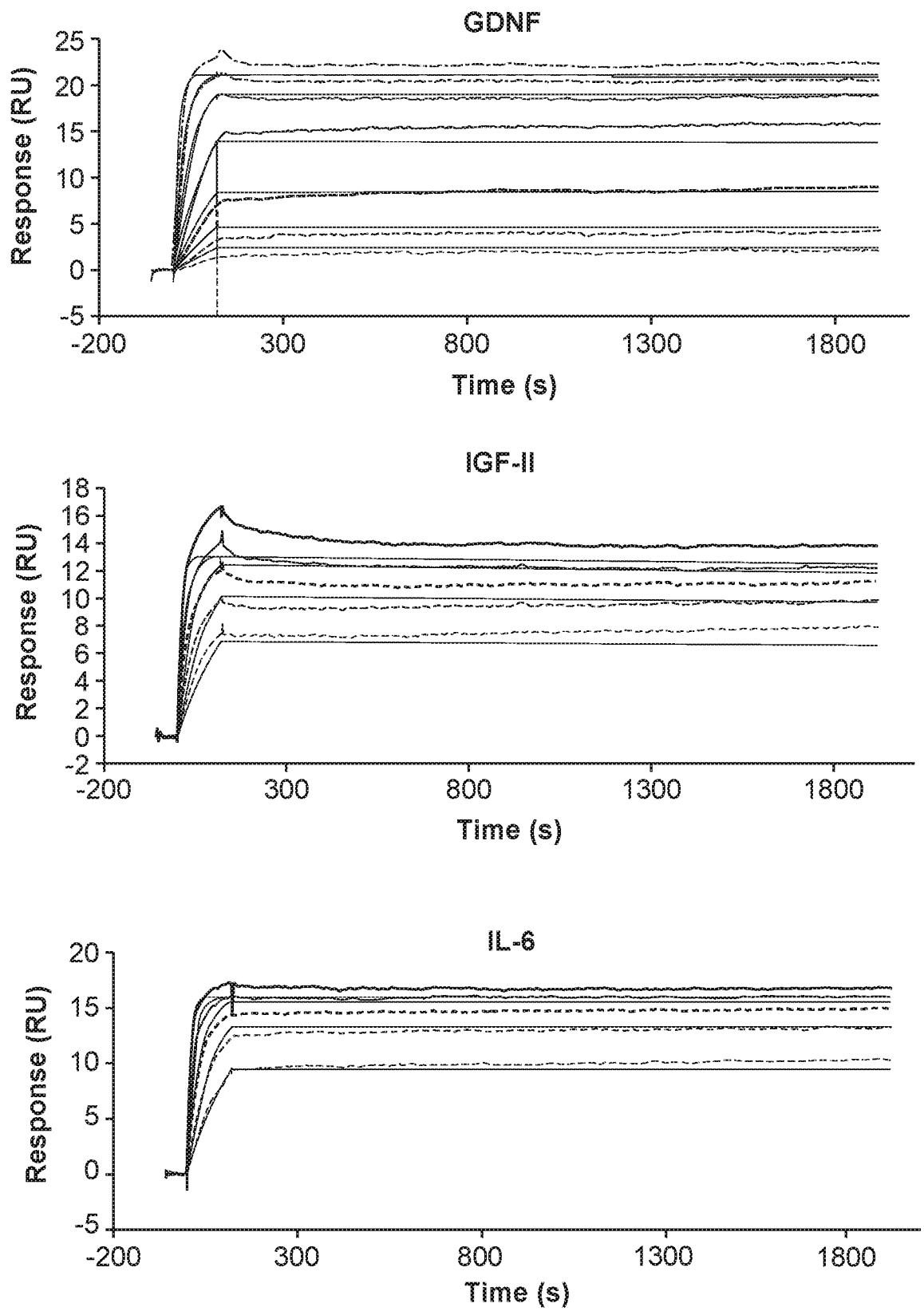
FIG. 10. 1:1 binding model fit to SPR data in Table 3.
Figure 10:
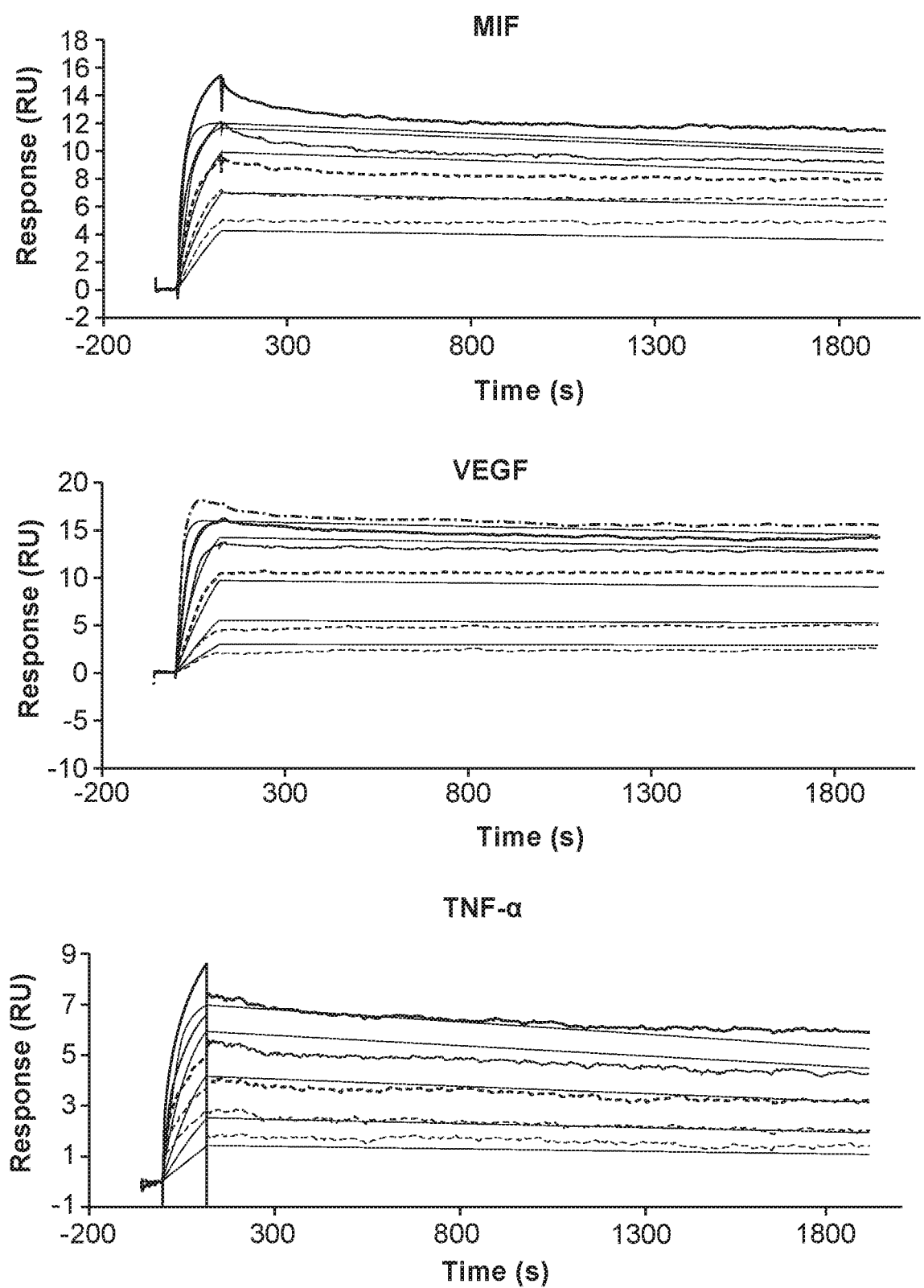

Kinetic analysis of affinity reagents. Knowledge about the kinetics of binding between antibodies and antigens is important for all immunoassays (3, 19). The relationship between kinetics and assay performance was explored. A previous report showed good correlation in traditional PLA between limit-of-detection and theoretical affinity, but did not determine equilibrium dissociation constants ($K_D$) for the antibodies used (11). Furthermore, no analyses have been reported on either association rate constants, $k_a$ (on-rates), or dissociation rate constants, $k_d$ (off-rates), and their significance in proximity ligation assays. To address this, surface plasmon resonance (SPR) (41) was used to determine $K_D$ values as well as on- and off-rates for the antibody-antigen interactions investigated. Kinetic parameters are listed in Table 2 and SPR sensorgrams for individual analytes fitted to a 1:1 binding model are provided in FIG. 10. The results are also summarized in an isoaffinity graph (FIG. 4a) where the two rate constants are plotted against each other to provide $K_D$ values along diagonal isoaffinity lines (42). The on-rates varied 30-fold from $4.9 \times 10^5$ $M^{-1}s^{-1}$ for IGF-II to $1.6 \times 10^7$ $M^{-1}s^{-1}$ for VEGF. Off-rates varied from $1.6 \times 10^{-4}$ $s^{-1}$ for TNF-α to exceptionally slow off-rates below the sensitivity range of the Biacore T200 instrument ($1.0 \times 10^{-5}$ $s^{-1}$) for both GDNF and IL-6. The software used to fit the data still provided off-rates beyond the limit of the instrument (results in Table 3) but because of uncertainty in the accuracy, off-rates were limited to no lower than $1.0 \times 10^{-5}$ $s^{-1}$ in the calculation of $K_D$. The resulting $K_D$ values spanned more than 2 orders of magnitude, ranging from $2.8 \times 10^{-10}$ M for TNF-α to below $7.1 \times 10^{-13}$ M for GDNF.

TABLE 2

Summary of kinetic analysis data for six biomarkers using SPR.

| Analyte | Association rate constant $k_a$ [$M^{-1}$ $s^{-1}$] | Dissociation rate constant $k_d$ [$s^{-1}$] | Equilibrium dissociation constant $K_D$ [M] |
|---|---|---|---|
| GDNF | 1.4E+07 | <1.0E−05 | <7.1E−13 |
| IL-6 | 2.3E+06 | <1.0E−05 | <4.3E−12 |
| VEGF | 1.6E+07 | 5.6E−05 | 3.6E−12 |
| IGF-II | 4.9E+05 | 2.5E−05 | 5.1E−11 |

TABLE 2-continued

Summary of kinetic analysis data for six biomarkers using SPR.

| Analyte | Association rate constant $k_a$ [M$^{-1}$ s$^{-1}$] | Dissociation rate constant $k_d$ [s$^{-1}$] | Equilibrium dissociation constant $K_D$ [M] |
|---------|------|------|------|
| MIF | 1.1E+06 | 9.4E−05 | 8.3E−11 |
| TNF-α | 5.7E+05 | 1.6E−04 | 2.8E−10 |

Figure 11:
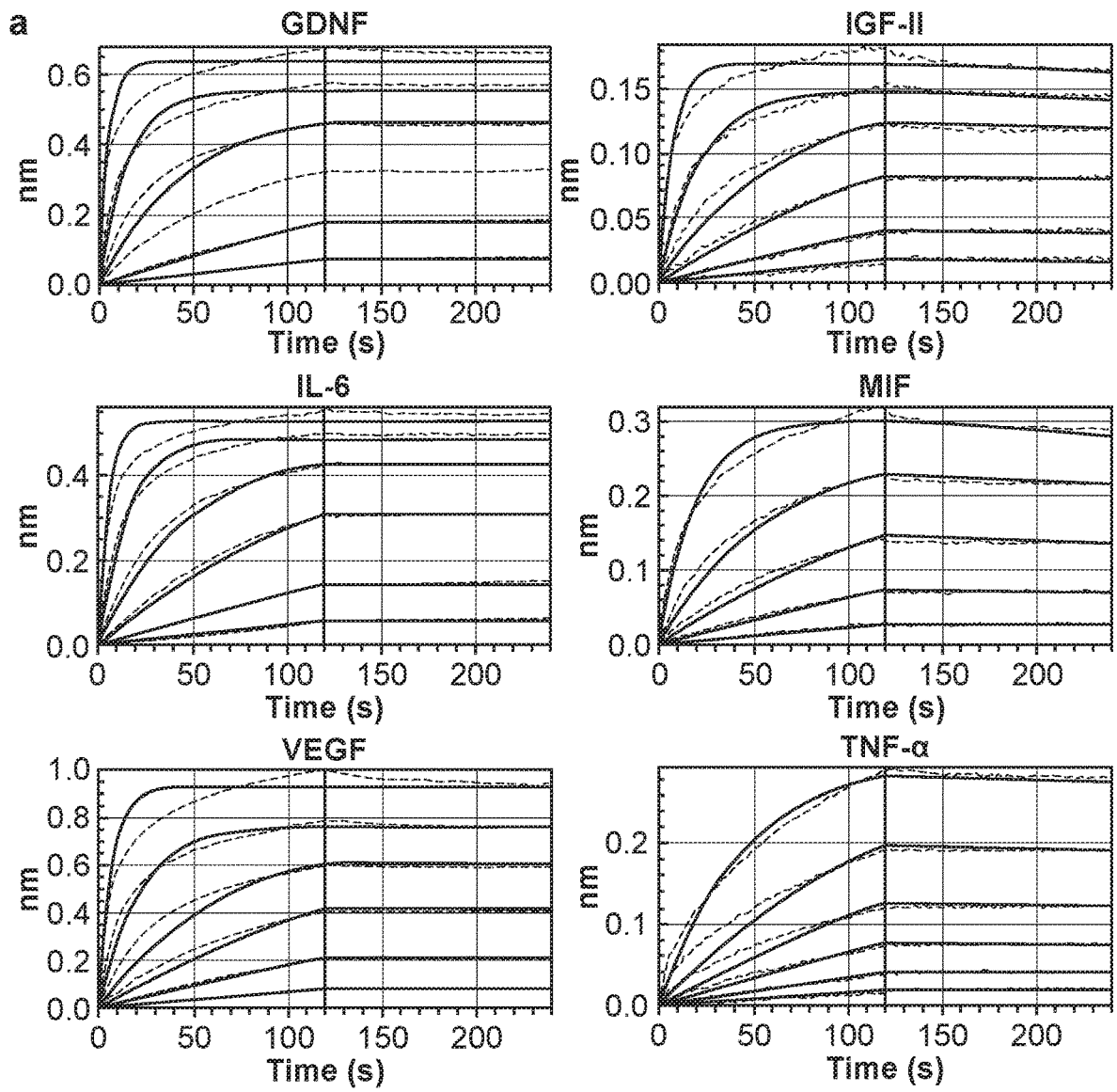
FIG. 11. Kinetic analysis using BLI. 1:1 binding model fit to BLI data in Table 4 (a). Isoaffinity graph for six analytes determined by BLI (b). Isoaffinity lines for various $K_D$ values are shown as diagonal lines.

Because some of the off-rates determined by SPR were found to be below the sensitivity range of the Biacore instrument complementary analysis was performed using biolayer interferometry (BLI) (43). These measurements corroborated the SPR results; off-rates for GDNF and IL-6 were also beyond the sensitivity of the Fortebio Octet RED instrument. Kinetic data for BLI measurements, binding curves for individual analytes fitted to a 1:1 binding model, and an isoaffinity chart for all analytes are provided in FIG. 11. $K_D$ values determined by BLI varied more than 3 orders of magnitude, ranging from 6.4×10$^{-9}$ M for TNF-α to below 2.5×10$^{-12}$ M for GDNF and IL-6. These values are approximately an order of magnitude higher than the corresponding SPR data, largely due to differences in the determination of on-rates. SPR is a flow-cell based method with a three-dimensional dextran matrix whereas BLI utilizes planar fiberoptic sensors in a well-plate format. It has previously been reported that the BLI system underestimates fast on-rates due to mass-transfer limitations, which is consistent with earlier findings (44). The numeric values of kinetic constants determined by surface-based methods are likely to differ from solution-based values which are presumably more applicable to homogenous PLA. Nonetheless the relative rankings between the two methods display good agreement and are important indicators of comparative antibody quality.

All proximity-probes described in this work originate from affinity-purified polyclonal antibodies. These antibodies are mixtures derived from different cell lineages producing antibodies that recognize distinct epitopes of the antigen each with their own individual kinetic characteristics. Due to this heterogeneity, kinetic properties of polyclonal antibody are inherently difficult to characterize with precision and the derived kinetic constants and affinities are considered an average for the different subpopulations existing within a batch of antisera. One prospective effect is that extended incubation time between sample and proximity-probes will allow continued exchanges that progress towards higher affinity interactions.

Using kinetics data to improve c-PLA performance. The isoaffinity graph in FIG. 4a includes the kinetic information for all antibody-antigen interactions investigated, revealing a clear differentiation in affinities. The antibodies with the highest affinity are located in the upper left corner as they are characterized by low off-rates and high on-rates that result in low $K_D$ values. GDNF, VEGF and IL-6 antibodies have high affinity with $K_D$ values below 5 pM. Accordingly, these analytes provide sub-pM limits-of-detection in c-PLA and wide dynamic ranges of at least 4 orders of magnitude as seen in dose-response curves (FIG. 4b, dose-response curves derived from the same batches of antibodies and antigens as those used in FIG. 4a but not completely the same batches as those used in FIG. 3). The remaining analytes, MIF, TNF-α, and IGF-II are clustered together with $K_D$ values above 50 pM. Consequently, c-PLA for these analytes does not perform nearly as well exhibiting limits-of-detection in the pM range (or higher) and narrower dynamic ranges that are constrained by the lower affinity of the antibodies. This comparison demonstrates that the inherent difference in sensitivity and dynamic range among the six analytes is not entirely dependent on the assay design but rather is caused by the quality of the affinity reagents used. It is noted that the only biomarker for which c-PLA did not improve assay performance compared to t-PLA is GDNF, the analyte with the highest affinity. The improvements in limit-of-detection for c-PLA over t-PLA are also larger for the lowest affinity interactions (see Tables 1 & 2), indicating a trend towards increased benefits of c-PLA when only low affinity reagents are available.

Figure 12:
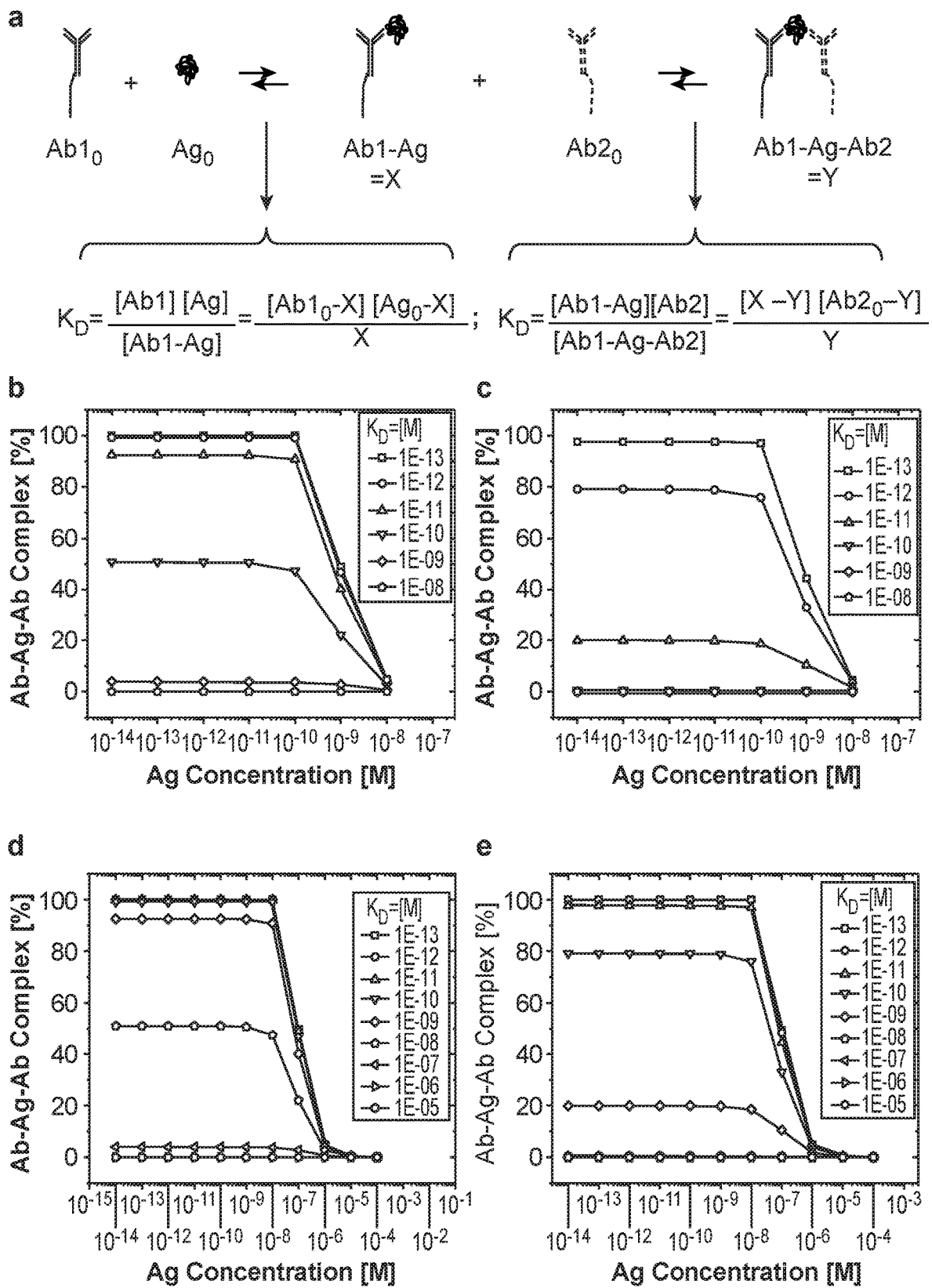
FIG. 12. Modeling of antibody-antigen-antibody complex formation at equilibrium. Equations used to determine the number of complexes formed (a). Fraction of antigens that form Ab-Ag-Ab complexes at equilibrium. Ab-Ag-Ab complexes formed after incubation of proximity-probes (2.5×10$^{-10}$ M) with antigen in 4 µL volume (b) and after addition of ligation cocktail containing the connector oligos and ligase in 124 µL volume (c). Ab-Ag-Ab complexes formed after incubation of proximity-probes (2.5×10$^{-8}$ M, 100-fold increase) with antigen in 4 µL volume (d) and after addition of ligation cocktail containing the connector oligos and ligase in 124 µL volume (e).

The detailed information obtained by kinetic analysis is beneficial for assay development as it suggests modifications that may result in improved signals. The kinetic constants were used to predict the number of complexes formed at equilibrium during sample incubation, and the new equilibrium that is established when the volume is increased by addition of the ligation mixture. Details are provided in the section named "Modeling of antibody-antigen-antibody complex formation at equilibrium" and FIG. 12. The calculations suggest that approximately 50% of the antigens present in solution are captured in a complex at equilibrium during sample incubation when the $K_D$ value of an interaction equals 1×10$^{-10}$ M (comparable to MIF and TNF-α, 8.3×10$^{-11}$ M and 2.8×10$^{-10}$ M respectively), (FIG. 12b). However, the subsequent addition of ligation mixture triggers complex dissociation until a new equilibrium is established. Modeling using $K_D$=1×10$^{-10}$ M indicates that at the new equilibrium essentially no antigens would remain in a complex resulting in no circle formation and consequently no detectable qPCR signal (FIG. 12c). Yet the assay still functions for analytes with these $K_D$ values, and the discrepancy is explained by suppressed dissociation as predicted by the low off-rates. The complex half-life ($t_{1/2}$) is defined as 1n 2/$k_d$ indicating that for both MIF and TNF-α (which have off-rates of approximately 1×10$^{-4}$ s$^{-1}$) it would take roughly 2 h for half of the complexes to dissociate. This is a sufficient duration to avoid significant losses during a 30 min ligation step (or 15 min in the case of t-PLA). In addition, these calculations do not consider any added advantages that the two circle-forming connector oligos have over t-PLA in retarding proximity-probe diffusion away from the analyte thereby facilitating antibody rebinding. DNA duplexes can be remarkably stable as exemplified by the SPR measurements, which employ DNA-directed immobilization of the capture agents. Previous studies have determined the off-rates for short oligonucleotides to range from 10$^{-4}$ s$^{-1}$ to below 10$^{-5}$ s$^{-1}$, values that are comparable or lower than the off-rates for the antibody-antigen interactions described in this work (45, 46). The calculations above highlight not only the benefits of high affinity probes in proximity ligation assays but also the importance of slow off-rates or other means to demote dissociation, especially when it entails large volume additions for ligation.

The large volume addition associated with ligation was originally introduced to minimize background ligation in t-PLA (12). Background ligation events in t-PLA occur when affinity probes and bridge oligo are randomly brought into close proximity. For c-PLA, the likelihood of background ligation is lower as this complex requires an additional connector oligo and two ligation events before producing a detectable signal. This results in less background and a better signal-to-noise ratio. Additional modeling studies provided in the FIG. 12e also indicate that higher proximity-probe concentrations result in more complex formation, which may increase signal-to-noise ratios even further. This is analogous to experimental findings on solid-phase where higher densities of surface-bound capture antibodies have shown to improve both limit-of-detection and dynamic range (47). Consequently, the combination of using a more stringent assay format like c-PLA with increased proximity-probe concentrations should improve assay performance with low affinity antibodies.

Figure 5:
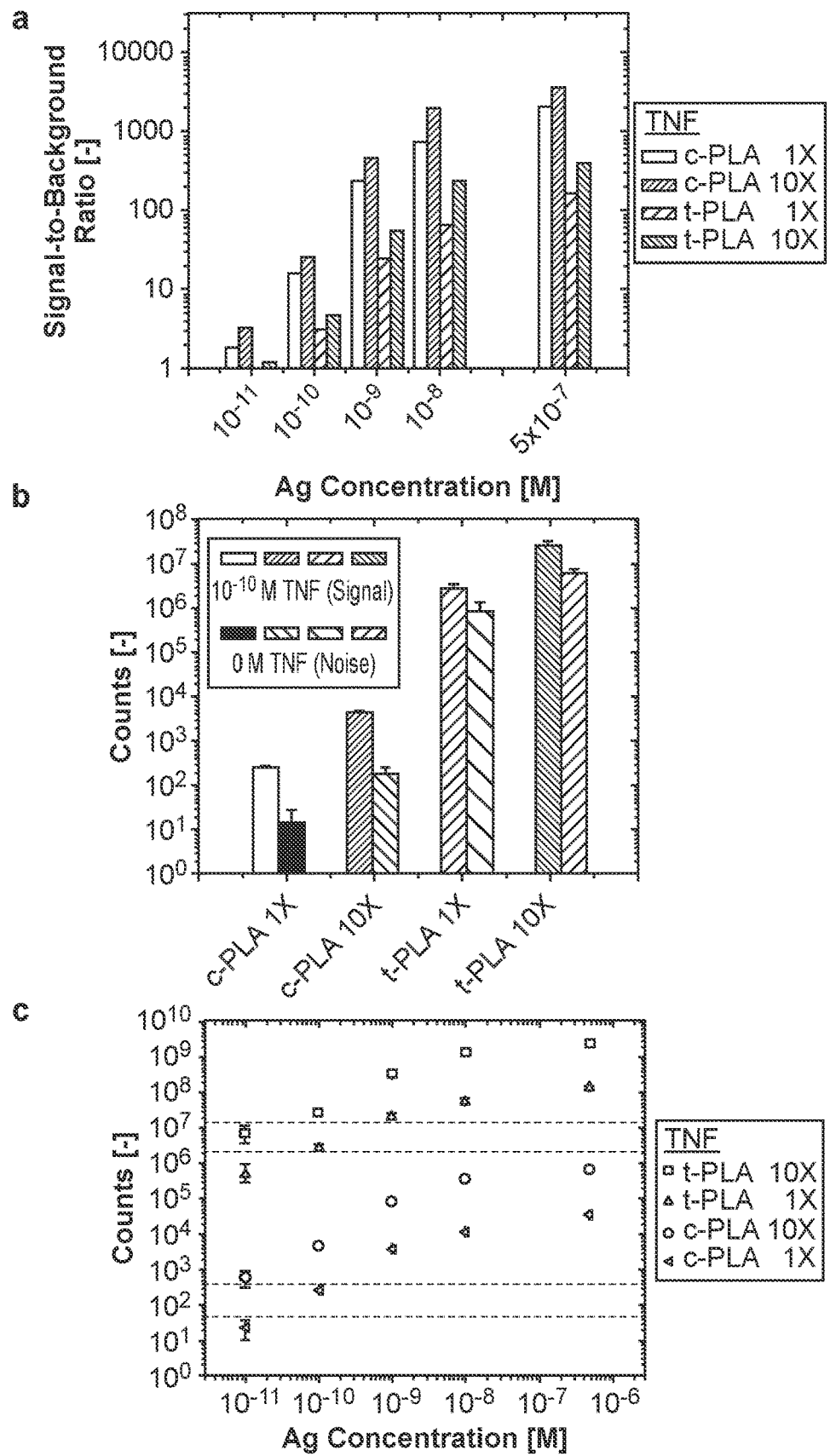
FIG. 5. Comparison of proximity ligation assay methods at different probe concentrations for TNF-α. a) Circular proximity ligation assay (c-PLA) results offer larger signal-to-background ratio than traditional PLA (t-PLA). b) Individual components for 100 pM signal-to-noise ratio. The greater signal-to-noise ratio for c-PLA is a consequence of higher stringency in c-PLA, which produces lower overall signals and larger differences between positive signal (100 pM) and negative background noise. c) Dose-response curves demonstrating that the higher signal-to-background ratios result in a more than 10-fold improvement in limit-of-detection (7 pM) for c-PLA when the probe concentrations are increased 10-fold compared to t-PLA (1×). Error bars denote one standard deviation (n=9) and the dashed lines denote limit-of-detection, defined as the mean signal of a blank sample+3 SD.

Stringency of c-PLA improves signal-to-background ratio and limit-of-detection. Based on simulations described above the impact of increased proximity-probe concentration for both traditional and circular PLA was tested. The TNF-α assay was chosen as it displayed the highest $K_D$ and $k_d$, providing a good example of low affinity reagents with fast off-rates. Both assay formats were performed with the standard affinity probe concentration (1×=0.25 nM) as well as a ten-fold increase. The results are shown in FIG. 5a and demonstrate a consistently higher signal-to-background ratio for c-PLA compared to t-PLA. The increase in signal-to-background ratio between the 10× and 1× affinity probe cases for the two methods is an expansion of the previous findings that probe concentration can be increased for low affinity interactions (12), though it is a complex subject that must be carefully balanced between antibody affinity and a higher probability of random background ligation (48). The greater signal-to-noise ratio for c-PLA is explained by a reduction in background noise as seen in FIG. 5b. This is a consequence of rigorous assay design in combination with exonuclease treatment, which effectively eliminates the background noise. Note that the higher stringency of c-PLA also lowers the signal but that the stability of circle-forming complexes combined with even lower background noise more than compensates for this decline. The higher signal-to-background ratio for c-PLA 10× improves limit-of-detection about one order of magnitude compared to the original t-PLA (FIG. 5c). Additional experiments suggest that the probe concentration can be increased even further for low affinity interactions, though it must be accompanied by an increase in the amount of connector oligonucleotides to ensure efficient circle formation.

c-PLA effectively detects proteins in human plasma. The results described thus far were all performed in buffer solutions as the goal was investigate the relationship between affinity and assay performance. Affinity analysis using SPR is not amenable to complex mixtures like plasma and although biolayer interferometry is less sensitive to matrix effects (43), both methods require pure ligands for accurate determination of kinetic constants. The correlation between kinetic constants and assay performance is established in FIG. 4 and provides valuable information for assay development. However, assay performance is known to differ greatly between different matrices and assay compatibility with complex mixtures is essential for diagnostic and clinical relevance (1).

Figure 6:
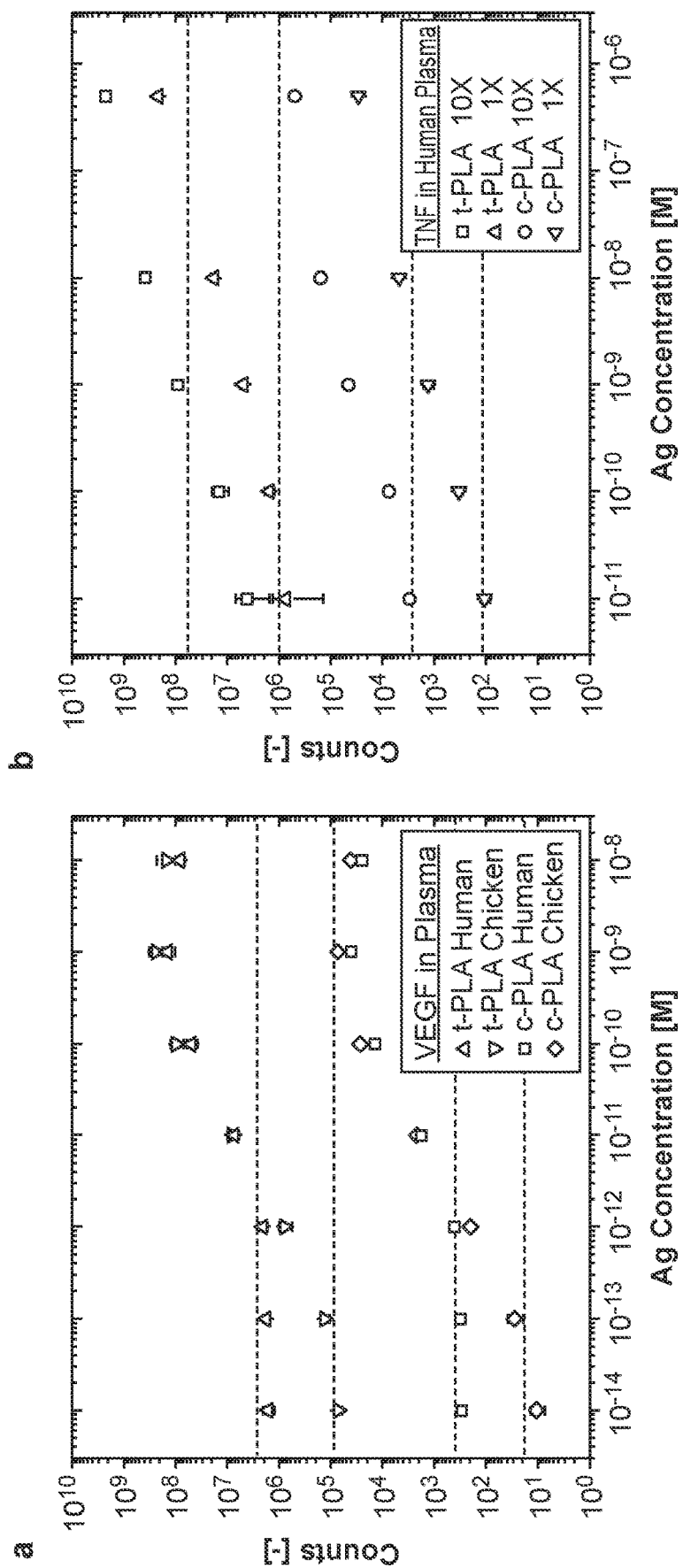
FIG. 6. Performance of proximity ligation assays in human plasma. a) Dose-response curves for VEGF detection demonstrate assay compatibility for both PLA methods in human and chicken plasma. The difference in limit-of-detection between the two matrices is attributed to endogenous VEGF levels in human plasma that are absent in chicken plasma. b) Dose-response curves for TNF-α detection in human plasma demonstrating improvement in assay performance for c-PLA over t-PLA. A 10-fold increase in probe concentration (10×=2.5 nM) improves reproducibility for c-PLA while there is no improvement for t-PLA. Error bars denote one standard deviation (n=9) and the dashed lines denote limit-of-detection, defined as the mean signal of a blank sample+3 SD.

It has been previously shown that multiplexed t-PLA enables quantitation of biomarkers in plasma samples (12-14). To determine the performance of c-PLA in a complex matrix, tested two analytes were tested: VEGF, as an example of a high affinity interaction (low $K_D$ and slow off-rates), and TNF-α, as an example of a low affinity interaction (high $K_D$ and fast off-rates). VEGF was effectively detected in human plasma by c-PLA down to physiological single-digit pM concentrations (12, 49) (FIG. 6a). Limit-of-detection is increased 100-fold from fM concentration in buffer to 1 pM for c-PLA and 2 pM for t-PLA in human plasma. Dynamic range is reduced accordingly by two orders of magnitude for both methods. Average CVs were lower for c-PLA than t-PLA, at 11% and 22% respectively, which is consistent with the findings in buffer solutions. These results confirm that the c-PLA provides less variation in a simplified assay format without the need for preamplification. Additional experiments were performed with VEGF in chicken plasma (in which human VEGF is absent) to verify that the changes in limit-of-detection and dynamic range are not impeded by the assay format, but are rather an effect of naturally occurring background levels of VEGF in human plasma (FIG. 6a). In chicken plasma fM limit-of-detection was achieved and more than four orders of magnitude dynamic range, which more closely reflects the original measurements in buffer solution. Hence both PLA methods are compatible with complex mixtures like human plasma with additional benefits in assay performance for c-PLA.

The advantages in assay performance of c-PLA over t-PLA for TNF-α (a low affinity interaction) also persist in human plasma (FIG. 6b). The limit-of-detection for c-PLA is about 10 pM for both 1× and 10× proximity-probe concentrations with lower CVs for the higher probe concentration (8% for 10× vs. 16% for 1×), presumably due to more efficient capture of antigens at the higher concentration. The limit-of-detection for t-PLA is approximately an order of magnitude higher compared to c-PLA, which reduces the dynamic range accordingly. CVs remain at around 30% across the linear range for both proximity-probe concentrations. In contrast to c-PLA, a 10-fold increase in proximity-probe concentration for t-PLA did not improve sensitivity (limit-of-detection about 700 pM), underscoring the challenges when using this method with low affinity antibodies. The ability to increase probe concentration in c-PLA also partially addresses the hook effect as it results in a later onset of proximity-probe saturation. Furthermore, statistical analysis of the CVs for TNF-α in plasma reveal that the lower CVs for c-PLA 10× are significantly different than CVs for c-PLA 1× as well as t-PLA 1× and 10× (p<0.001). The difference in CVs between c-PLA 1× and t-PLA 1× is also significant (p<0.001). This is encouraging as the generally accepted precision requirement for clinical immunoassays is below 20% (40, 50). These findings indicate that the increased stringency of c-PLA provides advantages over t-PLA in terms of ease of use and sensitivity while reducing variation. Most importantly, the opportunity to improve the performance of low affinity antibodies by simply increasing their concentration in c-PLA is maintained in complex matrices like plasma and serum.

Materials and Methods

Materials. Affinity-purified polyclonal antibodies and antigen targets were from R&D Systems. Product numbers are provided in the section named "Antibodies and Antigens". All oligonucleotides were from Integrated DNA Technologies. Sequences are listed in the section named "DNA sequences" and were kept the same for all analytes to allow for an unbiased comparison. Oligonucleotides used for proximity-probe conjugation were HPLC purified and designed to minimize probe-probe heteroduplex formation. All other reagents were from Sigma-Aldrich unless otherwise indicated.

Figure 7:
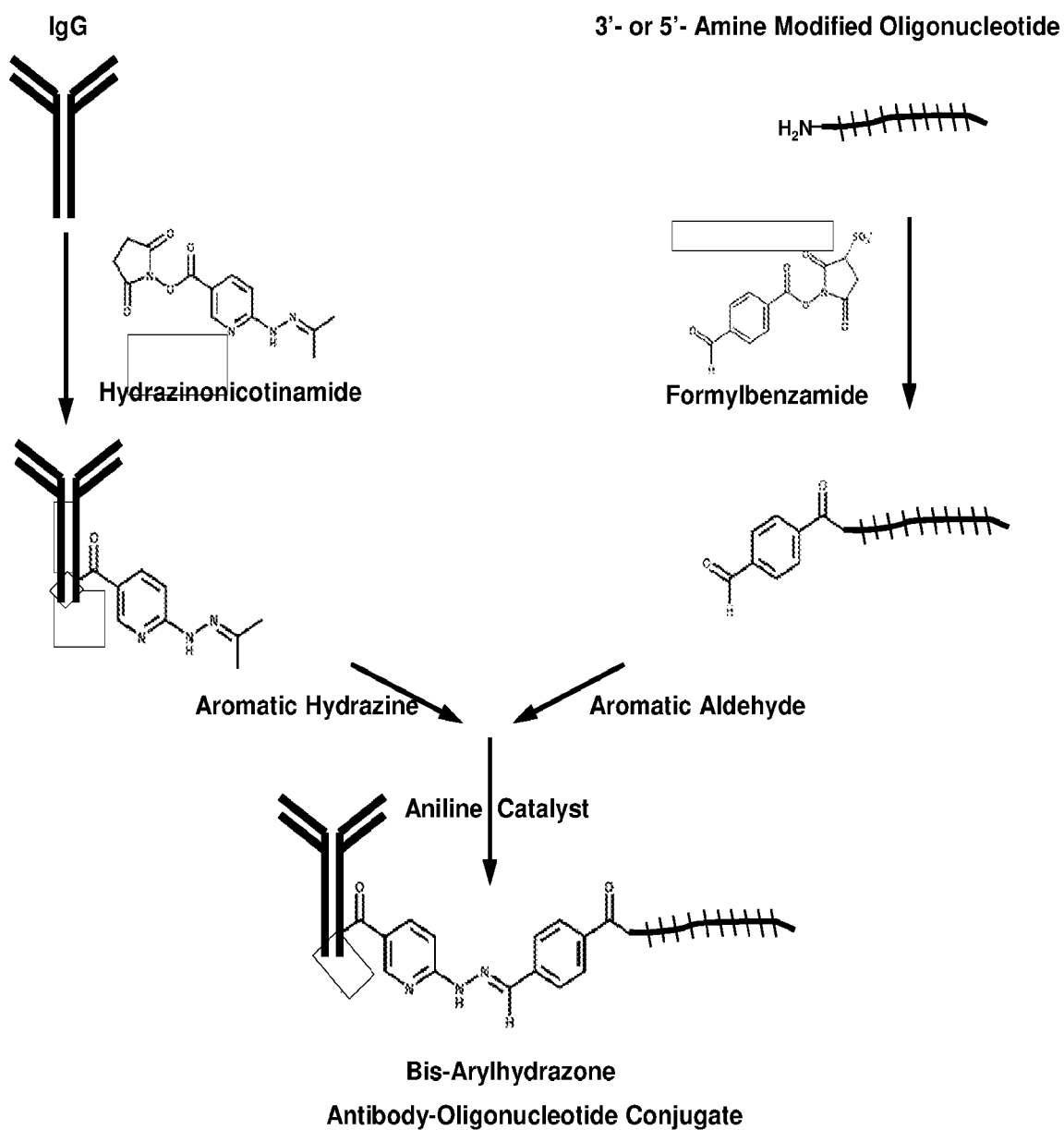
FIG. 7. Reaction scheme for proximity-probe conjugation. Antibodies are functionalized with an aromatic hydrazine. Oligonucleotides are functionalized with an aromatic aldehyde via amine-modifications on 5' or 3'-ends. Functionalized oligonucleotides are subsequently conjugated to the antibodies in the presence of an aniline catalyst.

Proximity-probe conjugation. Antibody-oligonucleotide conjugation was performed using hydrazone chemistry (Solulink) followed by purification according to the manufacturer's protocol (FIG. 7). One polyclonal antibody batch was divided into two portions and coupled to amine-modified oligonucleotides containing either a free phosphorylated 5'-end or a free 3'-end. Antibody-oligonucleotide conjugates were analyzed on a 2100 Agilent Bioanalyzer using the protein 80 kit under reducing conditions following the manufacturer's protocol. The estimated yield for all conjugates varied between 0.65 to 1.35 oligonucleotides per antibody. Final antibody-oligonucleotide concentration was determined using a Bradford protein assay (Bio-Rad) according to the manufacturer's specification. Antibody-oligo probes were diluted to 5 nM in 1× PBS supplemented with 2 mM EDTA (Thermo Fisher Scientific); 0.10% BSA; 0.02% $NaN_3$ and was stored at 4° C.

Proximity-probe target incubation. 2 µL of sample (diluted in either 1× PBS with 0.1% BSA or neat plasma from chicken or human (Sigma)) was added to 2 µL of proximity-probe mix and incubated for 2 hours at 37° C. to establish complex formation between the target analyte and antibodies in proximity-probes. The combined 4 µL incubation mixture contained a final concentration of 250 pM for each proximity-probe and was supplemented with 0.35 mg/mL polyadenylic acid potassium salt; 1% BSA; 0.1% Triton X-100; 0.05% IgG; 0.01% aprotinin; 1 mM phenylmethanesulfonyl fluoride; and 4 mM EDTA (Thermo Fisher Scientific) in 0.375× PBS.

Ligation step for circular PLA. 120 µL of ligation mixture was added to each 4 µL sample and incubated for 30 min at 45° C. The ligation mixture contained 100 nM each of the two circle-forming connector oligos; 0.025 U/µL Ampligase (Epicentre); 0.5 mM NAD; 1 mM DTT (Sigma-Aldrich); 0.01% Triton X-100; and 0.01% BSA in 20 mM Tris pH 8.4, 10 mM $MgCl_2$, and 50 mM KCl, (Thermo Fisher Scientific). Ligation was terminated by adding 10 µL of exonuclease mixture and incubated for 30 min at 37° C. followed by heat inactivation of exonuclease enzymes for 20 min at 80° C. Exonuclease mixture contained 2 U/µL exonuclease I (New England Biolabs); and 2 U/µL exonuclease III (New England Biolabs) in 1× NEBuffer 1 containing 10 mM Bis-Tris-Propane-HCl pH 7.0; 10 mM $MgCl_2$, and 1 mM DTT (New England Biolabs).

Ligation step for traditional PLA. 120 µL of ligation mixture was added to each 4 µL sample and incubated for 15 min at 30° C. The ligation mixture contained 100 nM t-PLA bridge oligo; 0.025 U/µL Ampligase (Epicentre); 0.25 mM NAD; 10 mM DTT; 0.02% Triton X-100; and 0.01% BSA in 20 mM Tris pH 8.4, 1.5 mM $MgCl_2$, and 50 mM KCl, (Thermo Fisher Scientific). Ligation was terminated by adding 2 µL of stop ligation mixture followed by a 5 min incubation at room temperature. The stop ligation mixture contained 0.125 U/µL Uracil-DNA Excision Mix (Epicentre) in 20 mM Tris pH 8.4, 50 mM KCl (Thermo Fisher Scientific).

Pre-amplification step for traditional PLA. 25 µL of the terminated ligation mixture was added to 25 µL preamplification mixture and cycled with the following conditions: 95° C. for 3 min (1 cycle); 95° C. for 30 s and 60° C. for 4 min (13 cycles) and a final hold at 4° C. The preamplification mixture contained 20 nM pre-amplification primers; 0.06 U/µL Platinum Taq DNA Polymerase (Thermo Fisher Scientific); and 1.6 mM dNTP Mix (Agilent Technologies) in 20 mM Tris pH 8.4, 6 mM $MgCl_2$, and 50 mM KCl, (Thermo Fisher Scientific). Following pre-amplification the product was diluted 10-fold in TE buffer and stored at 4° C. until qPCR quantification.

qPCR quantification and data analysis. 2 µL of either exonuclease-treated ligation product (for circular PLA) or diluted preamplification product (for traditional PLA) was added to qPCR master mix to a final volume of 10 µL containing 400 nM primers and 1× Power SYBR Green PCR Master Mix (Thermo Fisher Scientific). Samples were quantified using real time qPCR (ABI 7900 HT) with the following thermal cycling conditions: 95° C. for 10 min (1 cycle); 95° C. for 15 s and 60° C. for 60 s (40 cycles). Ct values were converted to an estimated number of ligated molecules using the formula $10^{-0.301 \times Ct + 11.439}$ as previously described (13). Experiments were performed with three biological replicates that were quantified in triplicate qPCR experiments generating nine data points per concentration analyzed. Limit-of-detection was derived relative to the blank sample where the dose-response curve and the dashed line (mean signal of a blank sample+3 standard deviations) intersects (40). Statistical analysis was performed using bootstrapping (random sampling with replacement on the independent measurements of biological replicates 1000 times).

Figure 9:
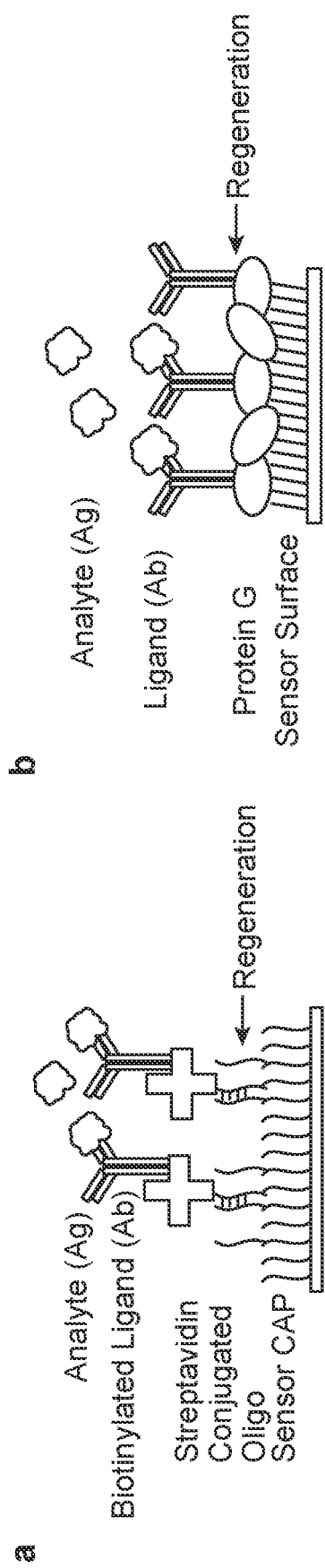
FIG. 9. Schematic of Biacore biotin CAP chip (a) and Fortebio protein G sensor (b).

Kinetic analysis using SPR. SPR analysis was performed at 25° C. using a Biacore T200 instrument and a Biotin CAPture Kit (GE Healthcare, FIG. 9a). All antibodies were biotinylated using EZ-Link NHS-PEO4-Biotin kit (Thermo Fisher Scientific) according to manufacturer's recommendation using a 1:1 mole ratio of biotin to antibody. Excess biotin was removed using Zeba spin columns to avoid interference with the binding of biotinylated antibodies to the surface of the CAP chip. Antibody immobilization was tailored to a level that resulted in a maximum analyte binding capacity ($R_{max}$) of 25-50 RU:s. Analytes were diluted in HBS-EP+ buffer and passed over the chip at a rate of 30 µL/min. Association was measured for 120 s and dissociation for 1800 s. Sensors were regenerated using a solution containing 6M Guanidine-HCl and 0.25M NaOH. Rate constants ($k_a$ and $k_d$) were determined using BIAevaluation software version 4.1 (Biacore) with a 1:1 model and global fitting of at least five concentrations in 2-fold dilution series ranging from 200 to 0 nM (Table 3 and FIG. 10). Affinity constants ($K_D$) were subsequently derived from the ratio of $k_a$ and $k_d$.

TABLE 3

Summary of kinetic constants obtained by SPR analysis.

| Analyte | $K_D$ (M) | $k_a$ ($M^{-1}s^{-1}$) | $k_d$ ($s^{-1}$) | SE ($k_a$) | SE ($k_d$) | $R_{max}$ (RU) | $Chi^2$ ($RU^2$) |
|---|---|---|---|---|---|---|---|
| GDNF | <7.1E−13 (1.73E−13) | 1.35E+07 | <1.0E−5 (2.34E−06)* | 16 | 1.7E−07 | 21.1 | 0.83 |
| IL-6 | <4.3E−12 (1.99E−13) | 2.33E+06 | <1.0E−5 (4.65E−07)* | 1.6E+03 | 5.7E−08 | 15.9 | 0.35 |
| VEGF | 3.60E−12 | 1.55E+07 | 5.57E−05 | 6.1E+04 | 4.2E−07 | 16.0 | 0.56 |
| IGF-II | 5.11E−11 | 4.86E+05 | 2.49E−05 | 6.3E+02 | 5.0E−07 | 13.1 | 0.85 |
| MIF | 8.26E−11 | 1.14E+06 | 9.41E−05 | 1.6E+03 | 6.3E−07 | 12.0 | 0.82 |
| TNF-α | 2.79E−10 | 5.67E+05 | 1.58E−04 | 1.5E+03 | 1.2E−07 | 7.3 | 0.64 |

*Off rates provided by the software were beyond the sensitivity range of the instrument.

Kinetic analysis using BLI. BLI analysis was performed on a Fortebio Octet RED instrument using protein G biosensors (Fortebio, FIG. 9b). All antibodies and analytes were diluted in assay buffer (0.1 mg/mL BSA and 0.13% Triton X-100 in 10 mM Tris pH 7.5, 1 mM CaCl2, and 150 mM NaCl). Antibody immobilization was tailored to a binding level of approximately 3.6 nm by varying the antibody loading time. All measurements were conducted at 30° C. in 200 μL total with constant agitation. Association was measured for 120 s and dissociation for 1200 s. Sensors were regenerated using a 10 mM glycine solution at pH 1.7. For each analyte, three replicates covering full kinetics cycles were performed and resulted in identical binding curves across all cycles. Rate constants (ka and kd) were determined using data analysis software version 8.2 (Fortebio) with a 1:1 model and global fitting of at least five concentrations in 3-fold dilution series ranging from 500 to 0 nM. Affinity constants (KD) were subsequently derived from the ratio of ka and kd. The results of the kinetic analysis by BLI are provided in Table 4 and FIG. 11.

TABLE 4

Summary of kinetic constants obtained by BLI analysis.

| Analyte | $K_D$ (M) | $k_a$ (M$^{-1}$s$^{-1}$) | $k_d$ (s$^{-1}$) | SE ($k_a$) | SE ($k_d$) | $R_{max}$ (RU) | Chi$^2$ (RU$^2$) |
|---|---|---|---|---|---|---|---|
| GDNF | <2.54E−12 | 3.93E+05 | <1.0E−06* | 6.57E+03 | 6.80E−07 | 0.638 | 0.757 |
| IL-6 | <2.49E−12 | 4.02E+05 | <1.0E−06* | 5.33E+03 | 4.32E−07 | 0.524 | 0.363 |
| VEGF | 5.70E−11 | 2.80E+05 | 1.60E−05 | 4.70E+03 | 4.25E−05 | 0.925 | 1.524 |
| IGF-II | 1.17E−09 | 2.74E+05 | 3.21E−04 | 3.60E+03 | 3.38E−05 | 0.171 | 0.034 |
| MIF | 1.75E−09 | 3.04E+05 | 5.32E−04 | 3.75E+03 | 3.54E−05 | 0.305 | 0.062 |
| TNF-α | 6.43E−09 | 4.29E+04 | 2.76E−04 | 6.91E+02 | 3.80E−05 | 0.311 | 0.070 |

*Off rates were beyond the sensitivity range of the instrument.

Antibodies and Antigens. Affinity reagents used were from R&D Systems and had the following product numbers for antibodies & antigens: GDNF: AF-212-NA & 212-GD-010; IL-6 AF-206-NA & 206-IL-010; VEGF: AF-293-NA & 293-VE-010; TNF-α: AF-210-NA & 210-TA-005; IGF-II: AF-292-NA & 292-G2-050; MIF: AF-289-PB & 289-MF-002.

DNA Sequences.

```
Proximity-probes used for both circular and traditional PLA
Ab-probe with phosphorylated 5'-end:
                                                    (SEQ ID NO: 1)
5'-/5Phos/TCACGGTAGCATAAGGTGCACGTTACCTTGATTCCCGTCC/3AmMO/-3'

Ab-probe with 3'-end:
                                                    (SEQ ID NO: 2)
5'-/5AmMC6/CATCGCCCTTGGACTAGCATACCCATGAACACAAGTTGCGTC

ACGATGAGACTGGATGAA-3'

Connector oligos used for circle formation in circular PLA
Connector-57:
                                                    (SEQ ID NO: 3)
5'-/Phos/TGCTACCGTCTTACCGAGCTTCTGTGATGATGAGGATGCTCACAT

CGAGCAACTTGT-3'

Connector-105:
                                                    (SEQ ID NO: 4)
5'-/Phos/GTTCATGGGATCCTTCATTCCACCGGTCCTTCATTCCACCGGTACGAGA

CGTGACGACTGCATTCCTTCATTCCACCGGTCCTTCATTCCACCGGTTGCACC

TTA-3' qPCR primers used for circular PLA
Forward Primer (P1):
                                                    (SEQ ID NO: 5)
5'-GCTCACATCGAGCAACTTGTGTT-3'

Reverse Primer (P2):
                                                    (SEQ ID NO: 6)
5'-AGCTCGGTAAGACGGTAGCATAA-3'
Note: Several different primer pairs were tested and it was found
that primers spanning ligation junction sites worked the best.
These primers were also used for c-PLA pre-amplification comparison.
```

```
-continued

Bridge oligo used for ligation in traditional PLA
                                                                 (SEQ ID NO: 7)
5'-CUACCGUGAUUCAUCCAG-3'

Pre-amplification primers used for traditional PLA
Forward Primer:
                                                                 (SEQ ID NO: 8)
5'-CATCGCCCTTGGACTAGCAT-3'

Reverse Primer:
                                                                 (SEQ ID NO: 9)
5'-GGACGGGAATCAAGGTAACG-3' qPCR primers used for traditional PLA
Forward Primer:
                                                                 (SEQ ID NO: 10)
5'-ACCCATGAACACAAGTTGCG-3'

Reverse Primer:
                                                                 (SEQ ID NO: 11)
5'-GGACGGGAATCAAGGTAACG-3'
```

Modeling of Antibody-Antigen-Antibody Complex Formation at Equilibrium.

Using parameters derived from kinetic analysis the formation of antibody-antigen-antibody (Ab-Ag-Ab) complexes was modeled at various conditions used in proximity ligation assay. This information is valuable to gain a better understanding of the assay and to support assay development for equilibrium and pre-equilibrium conditions, which often exist in cases of low analyte concentration and high affinity interactions. Using the equations described in FIG. 12 the fraction of antigens that form Ab-Ag-Ab complexes at equilibrium was modeled. This allows one to estimate the number of ligation events that may take place when the equilibrium dissociation constants ($K_D$) are varied from $10^{-13}$ to $10^{-8}$ M.

It is noted that these calculations only consider the formation of complexes and do not take into account whether it will result in a ligation event. For example ligation events will not be produced by complexes formed between analogous proximity-probes or when one of the antibodies in the complex lacks a conjugated oligo. Free oligonucleotides that may contribute to background ligation or stabilize formed complexes are also not considered in the calculations.

The following tables provide supporting data for graphs shown in the figures.

TABLE 5

FIG. 3a data.

| VEGF | c-PLA | | | | t-PLA | | | |
|---|---|---|---|---|---|---|---|---|
| Concentration [M] | Counts [—] | SD [—] | SBR [—] | CV [%] | Counts [—] | SD [—] | SBR [—] | CV [%] |
| 1.00E−08 | 4.83E+05 | 7.70E+04 | 16274 | 15.9 | 2.50E+09 | 2.87E+08 | 7230 | 11.5 |
| 1.00E−09 | 7.78E+05 | 1.28E+05 | 26204 | 16.4 | 3.98E+09 | 1.40E+09 | 11494 | 35.1 |
| 1.00E−10 | 9.59E+04 | 4.84E+03 | 3228 | 5.0 | 7.59E+08 | 1.35E+08 | 2193 | 17.7 |
| 1.00E−11 | 4.82E+03 | 6.50E+02 | 162 | 13.5 | 4.21E+07 | 5.94E+06 | 122 | 14.1 |
| 1.00E−12 | 6.19E+02 | 7.46E+01 | 21 | 12.1 | 3.69E+06 | 1.48E+06 | 11 | 40.0 |
| 1.00E−13 | 2.72E+02 | 8.42E+01 | 9.1 | 31.0 | 1.61E+06 | 6.34E+05 | 4.6 | 39.4 |
| 1.00E−14 | 2.03E+02 | 9.35E+01 | 6.8 | 46.1 | 5.95E+05 | 2.76E+05 | 1.7 | 46.3 |
| 0 | 2.97E+01 | 1.37E+01 | | 46.2 | 3.46E+05 | 6.36E+04 | | 18.4 |
| Average CV in Linear Range | | | | 15.6 | | | | 29.3 |

TABLE 6

FIG. 3b data.

| GDNF | c-PLA | | | | t-PLA | | | |
|---|---|---|---|---|---|---|---|---|
| Concentration [M] | Counts [—] | SD [—] | SBR [—] | CV [%] | Counts [—] | SD [—] | SBR [—] | CV [%] |
| 1.00E−08 | 2.14E+05 | 9.95E+03 | 14167 | 4.6 | 1.02E+09 | 2.25E+08 | 1519 | 22.0 |
| 1.00E−09 | 4.27E+05 | 2.11E+04 | 28266 | 4.9 | 2.24E+09 | 3.58E+08 | 3321 | 16.0 |
| 1.00E−10 | 5.94E+04 | 4.79E+03 | 3932 | 8.1 | 6.04E+08 | 1.05E+08 | 896 | 17.4 |
| 1.00E−11 | 3.34E+03 | 3.51E+02 | 221 | 10.5 | 6.06E+07 | 7.21E+06 | 90 | 11.9 |
| 1.00E−12 | 2.83E+02 | 7.36E+01 | 19 | 26.0 | 6.17E+06 | 8.33E+05 | 9.1 | 13.5 |
| 1.00E−13 | 1.72E+02 | 2.13E+01 | 11 | 12.4 | 7.19E+06 | 6.86E+06 | 11 | 95.4 |

TABLE 6-continued

FIG. 3b data.

| GDNF | c-PLA | | | | t-PLA | | | |
|---|---|---|---|---|---|---|---|---|
| Concentration [M] | Counts [—] | SD [—] | SBR [—] | CV [%] | Counts [—] | SD [—] | SBR [—] | CV [%] |
| 1.00E−14 | 1.70E+01 | 1.38E+01 | 1.1 | 81.1 | 1.92E+06 | 1.02E+06 | 2.8 | 53.3 |
| 0 | 1.51E+01 | 4.40E+00 | | 29.1 | 6.75E+05 | 1.70E+05 | | 25.2 |
| Average CV in Linear Range | | | | 12.4 | | | | 30.8 |

TABLE 7

FIG. 3c data.

| IL-6 | c-PLA | | | | t-PLA | | | |
|---|---|---|---|---|---|---|---|---|
| Concentration [M] | Counts [—] | SD [—] | SBR [—] | CV [%] | Counts [—] | SD [—] | SBR [—] | CV [%] |
| 1.00E−08 | 1.37E+05 | 1.02E+05 | 7545 | 74.7 | 2.05E+09 | 2.16E+09 | 1411 | 105.7 |
| 1.00E−09 | 3.12E+05 | 1.26E+05 | 17179 | 40.5 | 3.87E+09 | 2.75E+09 | 2667 | 71.1 |
| 1.00E−10 | 3.08E+04 | 5.96E+03 | 1700 | 19.3 | 3.88E+08 | 1.16E+08 | 267 | 29.9 |
| 1.00E−11 | 1.98E+03 | 3.69E+02 | 109 | 18.6 | 3.72E+07 | 1.28E+07 | 26 | 34.3 |
| 1.00E−12 | 1.41E+02 | 4.84E+01 | 7.8 | 34.3 | 1.16E+07 | 6.79E+06 | 8.0 | 58.7 |
| 1.00E−13 | 8.43E+01 | 7.41E+01 | 4.6 | 87.9 | 2.68E+06 | 1.29E+06 | 1.8 | 48.1 |
| 1.00E−14 | 5.52E+01 | 5.22E+01 | 3.0 | 94.5 | 3.03E+06 | 5.75E+05 | 2.1 | 19.0 |
| 0 | 1.81E+01 | 1.41E+01 | | 77.9 | 1.45E+06 | 4.83E+05 | | 33.3 |
| Average CV in Linear Range | | | | 28.2 | | | | 48.5 |

TABLE 8

FIG. 3d data.

| MIF | c-PLA | | | | t-PLA | | | |
|---|---|---|---|---|---|---|---|---|
| Concentration [M] | Counts [—] | SD [—] | SBR [—] | CV [%] | Counts [—] | SD [—] | SBR [—] | CV [%] |
| 3.00E−07 | 3.69E+04 | 1.50E+03 | 2168 | 4.1 | 4.66E+07 | 3.56E+06 | 24 | 7.6 |
| 1.00E−07 | 3.96E+04 | 1.08E+03 | 2326 | 2.7 | 5.20E+07 | 8.24E+06 | 27 | 15.9 |
| 1.00E−08 | 2.98E+04 | 1.25E+03 | 1749 | 4.2 | 3.97E+07 | 6.61E+06 | 21 | 16.7 |
| 1.00E−09 | 1.23E+04 | 7.11E+02 | 724 | 5.8 | 1.43E+07 | 1.80E+06 | 7 | 12.6 |
| 1.00E−10 | 1.02E+03 | 9.09E+01 | 60 | 8.9 | 1.84E+06 | 3.46E+05 | 1 | 18.8 |
| 1.00E−11 | 9.66E+01 | 2.18E+01 | 5.7 | 22.6 | 6.81E+05 | 7.59E+05 | 0.4 | 111.4 |
| 0 | 1.13E+01 | 5.67E+00 | | 50.3 | 1.70E+05 | 8.92E+04 | | 52.4 |
| Average CV in Linear Range | | | | 10.4 | | | | 39.9 |

TABLE 9

FIG. 3e data.

| TNF-a | c-PLA | | | | t-PLA | | | |
|---|---|---|---|---|---|---|---|---|
| Concentration [M] | Counts [—] | SD [—] | SBR [—] | CV [%] | Counts [—] | SD [—] | SBR [—] | CV [%] |
| 5.00E−07 | 3.30E+04 | 2.89E+03 | 2928 | 8.8 | 1.33E+08 | 1.23E+07 | 780 | 9.3 |
| 1.00E−08 | 1.16E+04 | 8.51E+02 | 1031 | 7.3 | 5.40E+07 | 5.99E+06 | 317 | 11.1 |
| 1.00E−09 | 3.70E+03 | 3.16E+02 | 328 | 8.5 | 1.98E+07 | 5.43E+06 | 116 | 27.5 |
| 1.00E−10 | 2.60E+02 | 1.45E+01 | 23 | 5.6 | 2.70E+06 | 6.61E+05 | 15.9 | 24.5 |
| 1.00E−11 | 2.21E+01 | 1.24E+01 | 2.0 | 56.3 | 4.43E+05 | 5.04E+05 | 2.6 | 113.8 |
| 1.00E−12 | 4.62E+00 | 2.54E+00 | 0.4 | 55.0 | 1.65E+06 | 5.39E+05 | 9.7 | 32.7 |
| 0 | 1.59E+01 | 1.18E+01 | | 74.2 | 8.29E+05 | 4.81E+05 | | 58.0 |
| Average CV in Linear Range | | | | 19.4 | | | | 44.2 |

TABLE 10

FIG. 3f data.

| IGF-II Concentration [M] | c-PLA Counts [—] | SD [—] | SBR [—] | CV [%] | t-PLA Counts [—] | SD [—] | SBR [—] | CV [%] |
|---|---|---|---|---|---|---|---|---|
| 1.00E−06 | 4.97E+04 | 3.14E+03 | 227 | 6.3 | 4.77E+07 | 4.72E+06 | 65 | 9.9 |
| 1.00E−07 | 5.03E+04 | 4.31E+03 | 230 | 8.6 | 5.89E+07 | 4.07E+06 | 81 | 6.9 |
| 1.00E−08 | 1.22E+04 | 2.15E+03 | 56 | 17.6 | 1.75E+07 | 2.90E+06 | 24 | 16.6 |
| 1.00E−09 | 5.27E+02 | 1.30E+02 | 2.4 | 24.7 | 6.41E+05 | 3.18E+05 | 0.9 | 49.5 |
| 1.00E−10 | 2.15E+02 | 1.39E+02 | 1.0 | 64.5 | 1.45E+05 | 1.98E+04 | 0.2 | 13.7 |
| 1.00E−11 | 1.71E+02 | 6.27E+01 | 0.8 | 36.7 | 4.00E+05 | 2.62E+05 | 0.5 | 65.6 |
| 0 | 2.19E+02 | 1.09E+02 | | 49.9 | 7.29E+05 | 6.10E+05 | | 83.7 |
| Average CV in Linear Range | | | | 17.0 | | | | 24.3 |

TABLE 11

FIG. 5 data.

| TNF-α Concentration [M] | c-PLA 1X Counts [—] | SD [—] | SBR [—] | CV [%] | c-PLA 10X Counts [—] | SD [—] | SBR [—] | CV [%] |
|---|---|---|---|---|---|---|---|---|
| 5.00E−07 | 3.30E+04 | 2.89E+03 | 2074 | 8.8 | 6.50E+05 | 8.32E+03 | 3552 | 1.3 |
| 1.00E−08 | 1.16E+04 | 8.51E+02 | 730 | 7.3 | 3.59E+05 | 2.13E+04 | 1961 | 5.9 |
| 1.00E−09 | 3.70E+03 | 3.16E+02 | 232 | 8.5 | 8.00E+04 | 5.97E+03 | 437 | 7.5 |
| 1.00E−10 | 2.60E+02 | 1.45E+01 | 16 | 5.6 | 4.62E+03 | 3.31E+02 | 25 | 7.2 |
| 1.00E−11 | 2.21E+01 | 1.24E+01 | 1.4 | 56.3 | 5.90E+02 | 2.82E+02 | 3.2 | 47.9 |
| 0 | 1.59E+01 | 1.18E+01 | | 74.2 | 1.83E+02 | 7.98E+01 | | 43.6 |
| Average CV in Linear Range | | | | 19.4 | | | | 17.1 |

| TNF-α Concentration [M] | t-PLA 1X Counts [—] | SD [—] | SBR [—] | CV [%] | t-PLA 10X Counts [—] | SD [—] | SBR [—] | CV [%] |
|---|---|---|---|---|---|---|---|---|
| 5.00E−07 | 1.33E+08 | 1.23E+07 | 160 | 9.3 | 2.24E+09 | 1.22E+08 | 392 | 5.4 |
| 1.00E−08 | 5.40E+07 | 5.99E+06 | 65 | 11.1 | 1.33E+09 | 9.22E+07 | 233 | 6.9 |
| 1.00E−09 | 1.98E+07 | 5.43E+06 | 24 | 27.5 | 3.20E+08 | 2.76E+07 | 56 | 8.6 |
| 1.00E−10 | 2.70E+06 | 6.61E+05 | 3.3 | 24.5 | 2.75E+07 | 4.09E+06 | 4.8 | 14.9 |
| 1.00E−11 | 4.43E+05 | 5.04E+05 | 0.5 | 113.8 | 7.03E+06 | 3.38E+06 | 1.2 | 48.1 |
| 0 | 8.29E+05 | 4.81E+05 | | 58.0 | 5.72E+06 | 2.22E+06 | | 38.9 |
| Average CV in Linear Range | | | | 44.2 | | | | 19.6 |

TABLE 12

FIG. 6a data.

| VEGF Concentration [M] | c-PLA Chicken Plasma Counts [—] | SD [—] | SBR [—] | CV [%] | c-PLA Human Plasma Counts [—] | SD [—] | SBR [—] | CV [%] |
|---|---|---|---|---|---|---|---|---|
| 1.00E−08 | 4.08E+04 | 1.83E+03 | 4425 | 4.5 | 2.48E+04 | 2.51E+03 | 96 | 10.2 |
| 1.00E−09 | 7.36E+04 | 4.79E+03 | 7975 | 6.5 | 4.05E+04 | 5.79E+03 | 156 | 14.3 |
| 1.00E−10 | 2.68E+04 | 1.10E+03 | 2905 | 4.1 | 1.38E+04 | 1.24E+03 | 53 | 9.0 |
| 1.00E−11 | 2.16E+03 | 1.18E+02 | 234 | 5.4 | 1.77E+03 | 1.81E+02 | 6.8 | 10.3 |
| 1.00E−12 | 1.98E+02 | 2.72E+01 | 22 | 13.7 | 4.08E+02 | 3.51E+01 | 1.6 | 8.6 |
| 1.00E−13 | 2.90E+01 | 9.48E+00 | 3.1 | 32.7 | 3.10E+02 | 1.26E+01 | 1.2 | 4.1 |
| 1.00E−14 | 1.07E+01 | 3.33E+00 | 1.2 | 31.1 | 2.92E+02 | 3.43E+01 | 1.1 | 11.8 |
| 0 | 9.23E+00 | 2.65E+00 | | 28.8 | 2.59E+02 | 4.46E+01 | | 17.2 |
| Average CV in Linear Range | | | | 12.5 | | | | 10.5 |

| VEGF Concentration [M] | t-PLA Chicken Plasma Counts [—] | SD [—] | SBR [—] | CV [%] | t-PLA Human Plasma Counts [—] | SD [—] | SBR [—] | CV [%] |
|---|---|---|---|---|---|---|---|---|
| 1.00E−08 | 1.49E+08 | 7.71E+07 | 2230 | 51.6 | 8.23E+07 | 1.62E+07 | 51 | 19.7 |
| 1.00E−09 | 2.39E+08 | 8.30E+07 | 3577 | 34.7 | 1.40E+08 | 3.87E+07 | 86 | 27.5 |
| 1.00E−10 | 9.58E+07 | 2.67E+07 | 1432 | 27.8 | 4.90E+07 | 1.14E+07 | 30 | 23.3 |

TABLE 12-continued

FIG. 6a data.

| | | | | | | | | |
|---|---|---|---|---|---|---|---|---|
| 1.00E−11 | 7.94E+06 | 1.74E+06 | 119 | 22.0 | 7.15E+06 | 1.34E+06 | 4.4 | 18.7 |
| 1.00E−12 | 7.87E+05 | 2.29E+05 | 12 | 29.0 | 2.06E+06 | 3.73E+05 | 1.3 | 18.1 |
| 1.00E−13 | 1.33E+05 | 2.71E+04 | 2.0 | 20.4 | 1.79E+06 | 2.54E+05 | 1.1 | 14.2 |
| 1.00E−14 | 7.16E+04 | 1.13E+04 | 1.1 | 15.8 | 1.63E+06 | 4.13E+05 | 1.0 | 25.3 |
| 0 | 6.69E+04 | 6.13E+03 | | 9.2 | 1.63E+06 | 3.96E+05 | | 24.3 |
| Average CV in Linear Range | | | | 26.8 | | | | 21.9 |

TABLE 13

FIG. 6b data.

| TNF-α | c-PLA 1X Human Plasma | | | | c-PLA 10X Human Plasma | | | |
|---|---|---|---|---|---|---|---|---|
| Concentration [M] | Counts [—] | SD [—] | SBR [—] | CV [%] | Counts [—] | SD [—] | SBR [—] | CV [%] |
| 5.00E−07 | 2.88E+04 | 1.72E+03 | 383 | 6.0 | 4.95E+05 | 2.33E+04 | 230 | 4.7 |
| 1.00E−08 | 4.77E+03 | 4.22E+02 | 63 | 8.8 | 1.58E+05 | 1.04E+04 | 73 | 6.6 |
| 1.00E−09 | 1.31E+03 | 2.92E+02 | 17 | 22.3 | 4.54E+04 | 4.25E+03 | 21 | 9.4 |
| 1.00E−10 | 3.31E+02 | 4.52E+01 | 4.4 | 13.7 | 7.42E+03 | 7.03E+02 | 3.4 | 9.5 |
| 1.00E−11 | 1.05E+02 | 2.16E+01 | 1.4 | 20.5 | 2.97E+03 | 1.60E+02 | 1.4 | 5.4 |
| 1.00E−12 | 7.59E+01 | 2.07E+01 | 1.0 | 27.2 | 2.26E+03 | 1.73E+02 | 1.0 | 7.6 |
| 1.00E−13 | 8.37E+01 | 2.03E+01 | 1.1 | 24.3 | 2.03E+03 | 6.31E+02 | 0.9 | 31.1 |
| 0 | 7.53E+01 | 1.32E+01 | | 17.5 | 2.15E+03 | 2.42E+02 | | 11.2 |
| Average CV in Linear Range | | | | 16.3 | | | | 7.7 |

| TNF-α | t-PLA 1X Human Plasma | | | | t-PLA 10X Human Plasma | | | |
|---|---|---|---|---|---|---|---|---|
| Concentration [M] | Counts [—] | SD [—] | SBR [—] | CV [%] | Counts [—] | SD [—] | SBR [—] | CV [%] |
| 5.00E−07 | 2.12E+08 | 2.17E+07 | 892 | 10.2 | 2.25E+09 | 2.80E+08 | 198 | 12.4 |
| 1.00E−08 | 1.79E+07 | 2.27E+06 | 75 | 12.7 | 3.81E+08 | 4.34E+07 | 33 | 11.4 |
| 1.00E−09 | 4.96E+06 | 5.80E+05 | 21 | 11.7 | 8.87E+07 | 1.65E+07 | 7.8 | 18.6 |
| 1.00E−10 | 1.56E+06 | 3.20E+05 | 6.6 | 20.5 | 1.44E+07 | 5.21E+06 | 1.3 | 36.3 |
| 1.00E−11 | 7.45E+05 | 6.02E+05 | 3.1 | 80.7 | 4.13E+06 | 2.59E+06 | 0.4 | 62.6 |
| 1.00E−12 | 1.54E+05 | 9.20E+04 | 0.6 | 59.6 | 2.70E+07 | 3.42E+07 | 2.4 | 126.7 |
| 1.00E−13 | 2.03E+05 | 1.86E+05 | 0.9 | 91.8 | 1.36E+07 | 1.29E+07 | 1.2 | 94.7 |
| 0 | 2.38E+05 | 2.47E+05 | | 104.0 | 1.14E+07 | 1.51E+07 | | 132.5 |
| Average CV in Linear Range | | | | 31.4 | | | | 32.2 |

TABLE 14

FIG. 8 data.

| VEGF | c-PLA w/PreAmp | | | | t-PLA w/PreAmp | | | |
|---|---|---|---|---|---|---|---|---|
| Concentration [M] | Counts [—] | SD [—] | SBR [—] | CV [%] | Counts [—] | SD [—] | SBR [—] | CV [%] |
| 1.00E−08 | 8.14E+07 | 1.45E+07 | 1367 | 17.8 | 1.00E+09 | 1.30E+08 | 5683 | 13.0 |
| 1.00E−09 | 2.36E+08 | 1.26E+07 | 3968 | 5.3 | 1.19E+09 | 6.96E+07 | 6745 | 5.9 |
| 1.00E−10 | 6.02E+07 | 5.82E+06 | 1011 | 9.7 | 1.78E+08 | 2.75E+07 | 1013 | 15.4 |
| 1.00E−11 | 4.88E+06 | 4.87E+05 | 82 | 10.0 | 1.26E+07 | 3.23E+06 | 71 | 25.7 |
| 1.00E−12 | 5.16E+05 | 5.85E+04 | 8.7 | 11.4 | 1.26E+06 | 1.98E+05 | 7.1 | 15.7 |
| 1.00E−13 | 9.55E+04 | 2.15E+04 | 1.6 | 22.5 | 5.77E+05 | 8.31E+04 | 3.3 | 14.4 |
| 1.00E−14 | 9.02E+04 | 2.52E+03 | 1.5 | 2.8 | 3.63E+05 | 1.83E+05 | 2.1 | 50.4 |
| 0 | 5.96E+04 | 2.09E+04 | | 35.2 | 1.76E+05 | 4.45E+04 | | 25.3 |
| Average CV in Linear Range | | | | 11.8 | | | | 15.4 |

REFERENCES

1. Landegren U, et al. (2012) Opportunities for sensitive plasma proteome analysis. *Anal Chem* 84(4):1824-1830.
2. Kingsmore S F (2006) Multiplexed protein measurement: technologies and applications of protein and antibody arrays. *Nat Rev Drug Discov* 5(4):310-321.
3. Wild D ed (2013) *The Immunoassay Handbook* (Elsevier, Oxford).
4. Zhang H Q, Zhao Q, Li X F, & Le X C (2007) Ultrasensitive assays for proteins. *Analyst* 132(8):724-737.
5. Spengler M, Adler M, & Niemeyer C M (2015) Highly sensitive ligand-binding assays in pre-clinical and clinical applications: immuno-PCR and other emerging techniques. *Analyst* 140(18):6175-6194.
6. Sano T, Smith C L, & Cantor C R (1992) Immuno-PCR: Very sensitive antigen detection by means of specific antibody-DNA conjugates. *Science* 258(Oct. 2, 1992): 120-122.
7. Nam J-M, Thaxton C S, & Mirkin C A (2003) Nanoparticle-Based Bio-Bar Codes for the Ultrasensitive Detection of Proteins. *Science* 301:1884-1886.
8. Schweitzer B, et al. (2002) Multiplexed protein profiling on microarrays by rolling-circle amplification. *Nat Biotechnol* 20(4):359-365.
9. Xie S & Walton S P (2010) Development of a dual-aptamer-based multiplex protein biosensor. *Biosens Bioelectron* 25(12):2663-2668.
10. Fredriksson S, et al. (2002) Protein detection using proximity-dependent DNA ligation assays. *Nat Biotechnol* 20(4):473-477.
11. Gullberg M, et al. (2004) Cytokine detection by antibody-based proximity ligation. *Proc Natl Acad Sci USA* 101(22):8420-8424.
12. Fredriksson S, et al. (2007) Multiplexed protein detection by proximity ligation for cancer biomarker validation. *Nat Methods* 4(4):327-329.
13. Fredriksson S, et al. (2008) Multiplexed Proximity Ligation Assays to Profile Putative Plasma Biomarkers Relevant to Pancreatic and Ovarian Cancer. *Clin Chem* 54(3):582-589.
14. Chang S, et al. (2009) Identification of a biomarker panel using a multiplex proximity ligation assay improves accuracy of pancreatic cancer diagnosis. *J Transl Med* 7(1):105.
15. Lundberg M, et al. (2011) Multiplexed homogeneous proximity ligation assays for high throughput protein biomarker research in serological material. *Mol Cell Proteomics* 10(4):1-10.
16. Tate J & Ward G (2004) Interferences in Immunoassay. *Clin Biochem Rev* 25(2):105-120.
17. Kim J, Hu J, Sollie R S, & Easley C J (2010) Improvement of sensitivity and dynamic range in proximity ligation assays by asymmetric connector hybridization. *Anal Chem* 82(16):6976-6982.
18. Zhu L, et al. (2006) A sensitive proximity ligation assay for active PSA. *Biol Chem* 387(6):769-772.
19. Xie S, Moya C, Bilgin B, Jayaraman A, & Walton S P (2009) Emerging affinity-based techniques in proteomics. *Expert Rev Proteomics* 6(5):573-583.
20. Castro-López V, Elizalde J, Pacek M, Hijona E, & Bujanda L (2014) A simple and portable device for the quantification of TNF-α in human plasma by means of on-chip magnetic bead-based proximity ligation assay. *Biosens Bioelectron* 54(0):499-505.
21. Pai S, Ellington A D, & Levy M (2005) Proximity ligation assays with peptide conjugate 'burrs' for the sensitive detection of spores. *Nucleic Acids Res* 33(18):e162.
22. Schallmeiner E, et al. (2007) Sensitive protein detection via triple-binder proximity ligation assays. *Nat Methods* 4(2):135-137.
23. Tavoosidana G, et al. (2011) Multiple recognition assay reveals prostasomes as promising plasma biomarkers for prostate cancer. *Proc Natl Acad Sci USA* 108(21):8809-8814.
24. Zhang H, Li X-F, & Le X C (2012) Binding-induced DNA assembly and its application to yoctomole detection of proteins. *Anal Chem* 84(2):877-884.
25. Di Giusto D A, Wlassoff W A, Gooding J J, Messerle B A, & King G C (2005) Proximity extension of circular DNA aptamers with real-time protein detection. *Nucleic Acids Res* 33(6):e64.
26. Jarvius J, et al. (2006) Digital quantification using amplified single-molecule detection. *Nat Methods* 3(9):725-727.
27. Soderberg O, et al. (2006) Direct observation of individual endogenous protein complexes in situ by proximity ligation. *Nat Methods* 3(12):995-1000.
28. Lundberg M, Eriksson A, Tran B, Assarsson E, & Fredriksson S (2011) Homogeneous antibody-based proximity extension assays provide sensitive and specific detection of low-abundant proteins in human blood. *Nucleic Acids Res* 39(15):e102.
29. Ericsson O, et al. (2008) A dual-tag microarray platform for high-performance nucleic acid and protein analyses. *Nucleic Acids Res* 36(8):e45.
30. Gómez de la Torre T Z, et al. (2012) Sensitive Detection of Spores Using Volume-Amplified Magnetic Nanobeads. *Small* 8(14):2174-2177.
31. Ke R, Nong R Y, Fredriksson S, Landegren U, & Nilsson M (2013) Improving Precision of Proximity Ligation Assay by Amplified Single Molecule Detection. *PLoS ONE* 8(7):e69813.
32. Hardenbol P, et al. (2003) Multiplexed genotyping with sequence-tagged molecular inversion probes. *Nat Biotechnol* 21(6):673-678.
33. Gold L, et al. (2010) Aptamer-Based Multiplexed Proteomic Technology for Biomarker Discovery. *PLoS ONE* 5(12):e15004.
34. Das S, et al. (2015) A general synthetic approach for designing epitope targeted macrocyclic peptide ligands. *Angew Chem Int Ed Engl* 54(45):13219-13224.
35. Tsai C-t, Robinson P V, Spencer C A, & Bertozzi C R (2016) Ultrasensitive Antibody Detection by Agglutination-PCR (ADAP). *ACS Cent Sci* 2(3):139-147.
36. Albayrak C, et al. (2016) Digital Quantification of Proteins and mRNA in Single Mammalian Cells. *Molecular Cell* 61(6):914-924.
37. Darmanis S, et al. (2010) Sensitive Plasma Protein Analysis by Microparticle-based Proximity Ligation Assays. *Molecular & Cellular Proteomics* 9(2):327-335.
38. Rissin D M, et al. (2010) Single-molecule enzyme-linked immunosorbent assay detects serum proteins at subfemtomolar concentrations. *Nat Biotech* 28(6):595-599.
39. Todd J, et al. (2007) Ultrasensitive Flow-based Immunoassays Using Single-Molecule Counting. *Clinical Chemistry* 53(11):1990-1995.
40. Armbruster D A & Pry T (2008) Limit of blank, limit of detection and limit of quantitation. *Clin Biochem Rev* 29(Suppl 1):S49-S52.
41. Cooper M A (2002) Optical biosensors in drug discovery. *Nat Rev Drug Discov* 1(7):515-528.
42. Markgren P-O, et al. (2002) Relationships between structure and interaction kinetics for HIV-1 protease inhibitors. *J Med Chem* 45(25):5430-5439.
43. Concepcion J, et al. (2009) Label-free detection of biomolecular interactions using biolayer interferometry for kinetic characterization. *Comb Chem High Throughput Screen* 12(8):791-800
44. Estep P, et al. (2013) High throughput solution-based measurement of antibody-antigen affinity and epitope binning. *mAbs* 5(2):270-278.
45. Gotoh M, Hasegawa Y, Shinohara Y, Shimizu M, & Tosu M (1995) A new approach to determine the effect of mismatches on kinetic parameters in DNA hybridization using an optical biosensor. *DNA Res* 2(6):285-293.
46. Liebermann T, Knoll W, Sluka P, & Herrmann R (2000) Complement hybridization from solution to surface-attached probe-oligonucleotides observed by surface-plasmon-field-enhanced fluorescence spectroscopy. *Colloids Surf A Physicochem Eng Asp* 169(1-3):337-350.
47. Fan R, et al. (2008) Integrated barcode chips for rapid, multiplexed analysis of proteins in microliter quantities of blood. *Nat Biotechnol* 26(12):1373-1378.
48. Hansen M C, Nederby L, Henriksen M O B, Hansen M, & Nyvold C G (2014) Sensitive ligand-based, protein quantification using immuno-PCR: A critical review of single-probe and proximity ligation assays. *Biotechniques* 56(5):217-227.
49. Larsson A, Sköldenberg E, & Ericson H (2002) Serum and plasma levels of FGF-2 and VEGF in healthy blood donors. *Angiogenesis* 5(1):107-110.
50. Andreasson U, et al. (2015) A Practical Guide to Immunoassay Method Validation. *Frontiers in Neurology* 6(179).
51. Bradbury A & Plückthun A (2015) Reproducibility: Standardize antibodies used in research. *Nature* 518:27-29.
52. Shen F, et al. (2011) Digital Isothermal Quantification of Nucleic Acids via Simultaneous Chemical Initiation of Recombinase Polymerase Amplification Reactions on SlipChip. *Analytical Chemistry* 83(9):3533-3540.
53. Yeh E-C, et al. (2017) Self-powered integrated microfluidic point-of-care low-cost enabling (SIMPLE) chip. *Sci Adv.* 3(3):e1501645.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations where it is desirable to examine analytes. Accordingly, the claims set forth below should be construed in view of the full breadth and spirit of the invention as disclosed herein.

What is claimed is:

1. A method for sample analysis comprising:
 (a) incubating a sample of blood plasma or serum comprising a target analyte that is at a concentration of less than 100 nM with:
  (i) a first conjugate comprising a binding agent and a first splint oligonucleotide, and
  (ii) a second conjugate comprising a binding agent and a second splint oligonucleotide,
  wherein the first and second conjugates are a polyclonal antibody that has been affinity purified, split into a first portion and a second portion, and then conjugated to the first and second splint oligonucleotides, under conditions suitable for binding of the binding agents of the first and second conjugates to the target analyte, to produce a product;
 (b) incubating at least some of the product of step (a) with:
  (i) a set of probes that produces a ligatable circle only when the probes are hybridized to the first and second splint oligonucleotides; and
  (ii) a ligase;
  to produce a reaction mix comprising covalently closed circular molecules;
 (c) treating at least some of the reaction mix of step (b) with an exonuclease to terminate the ligation and degrade any nucleic acid that is not a covalently closed circular molecule; and
 (d) after step (c), quantifying the amount of covalently closed circular molecules produced in step (b).

2. The method of claim 1, wherein the first and second conjugates bind to the target analyte with a low affinity.

3. The method of claim 1, wherein the quantifying step (d) is done by quantitative PCR, digital PCR, by hybridization to a microarray or by sequencing.

4. The method of claim 3, wherein the primers used for the quantitative PCR target the ligation junctions in the covalently closed circular molecules of (d).

5. The method of claim 1, wherein step (d) comprises amplifying the covalently closed circular molecules by rolling circle amplification (RCA) to produce RCA products.

6. The method of claim 5, wherein the method comprises counting the RCA products.

7. The method of claim 1, wherein the reactions of steps (a)-(c) are done in the same vessel.

8. The method of claim 7, wherein step (b) comprises adding the set of probes and ligase to the vessel comprising the product of step (a), and step (c) comprises adding one or more exonucleases to the vessel comprising the ligation product of step (b).

9. The method of claim 1, wherein:
 (i) the sample comprises a plurality of target analytes,
 (ii) step (a) comprises incubating the sample with multiple pairs of said first and second conjugates, wherein each pair of conjugates binds to a different target analyte; and
 (iii) step (d) comprises quantifying the number of covalently closed circular molecules corresponding to each target analyte.

10. The method of claim 1, wherein the target analyte is a protein.

11. The method of claim 1, wherein:
 at least two members of the set of probes of step (b)(i) each have a molecular index; and
 step (d) is done by i. sequencing the covalently closed circular molecules and then ii counting the number of covalently closed circular molecules using the index sequence.

12. The method of claim 1, wherein the target analyte is a cytokine.

* * * * *

SEQUENCE LISTING

```
<160> NUMBER OF SEQ ID NOS: 11

<210> SEQ ID NO 1
<211> LENGTH: 40
<212> TYPE: DNA
<213> ORGANISM: artificial sequences
<220> FEATURE:
<223> OTHER INFORMATION: synthetic oligonucleotide

<400> SEQUENCE: 1
tcacggtagc ataaggtgca cgttaccttg attcccgtcc                          40

<210> SEQ ID NO 2
<211> LENGTH: 60
<212> TYPE: DNA
<213> ORGANISM: artificial sequences
<220> FEATURE:
<223> OTHER INFORMATION: synthetic oligonucleotide

<400> SEQUENCE: 2
catcgccctt ggactagcat acccatgaac acaagttgcg tcacgatgag actggatgaa   60

<210> SEQ ID NO 3
<211> LENGTH: 57
<212> TYPE: DNA
<213> ORGANISM: artificial sequences
<220> FEATURE:
<223> OTHER INFORMATION: synthetic oligonucleotide

<400> SEQUENCE: 3
tgctaccgtc ttaccgagct tctgtgatga tgaggatgct cacatcgagc aacttgt      57

<210> SEQ ID NO 4
<211> LENGTH: 105
<212> TYPE: DNA
<213> ORGANISM: artificial sequences
<220> FEATURE:
<223> OTHER INFORMATION: synthetic oligonucleotide

<400> SEQUENCE: 4
gttcatggga tccttcattc caccggtcct tcattccacc ggtacgagac gtgacgactg   60
```
cattccttca ttccaccggt ccttcattcc accggttgca cctta         105

<210> SEQ ID NO 5
<211> LENGTH: 23
<212> TYPE: DNA
<213> ORGANISM: artificial sequences
<220> FEATURE:
<223> OTHER INFORMATION: synthetic oligonucleotide

<400> SEQUENCE: 5
gctcacatcg agcaacttgt gtt         23

<210> SEQ ID NO 6
<211> LENGTH: 23
<212> TYPE: DNA
<213> ORGANISM: artificial sequences
<220> FEATURE:
<223> OTHER INFORMATION: synthetic oligonucleotide

<400> SEQUENCE: 6
agctcggtaa gacggtagca taa         23

<210> SEQ ID NO 7
<211> LENGTH: 18
<212> TYPE: RNA
<213> ORGANISM: artificial sequences
<220> FEATURE:
<223> OTHER INFORMATION: synthetic oligonucleotide

<400> SEQUENCE: 7
cuaccgugau ucauccag         18

<210> SEQ ID NO 8
<211> LENGTH: 20
<212> TYPE: DNA
<213> ORGANISM: artificial sequences
<220> FEATURE:
<223> OTHER INFORMATION: synthetic oligonucleotide

<400> SEQUENCE: 8
catcgccctt ggactagcat         20

<210> SEQ ID NO 9
<211> LENGTH: 20
<212> TYPE: DNA
<213> ORGANISM: artificial sequences
<220> FEATURE:
<223> OTHER INFORMATION: synthetic oligonucleotide

<400> SEQUENCE: 9
ggacgggaat caaggtaacg         20

<210> SEQ ID NO 10
<211> LENGTH: 20
<212> TYPE: DNA
<213> ORGANISM: artificial sequences
<220> FEATURE:
<223> OTHER INFORMATION: synthetic oligonucleotide

<400> SEQUENCE: 10
acccatgaac acaagttgcg         20

<210> SEQ ID NO 11
<211> LENGTH: 20
<212> TYPE: DNA

```
<213> ORGANISM: artificial sequences
<220> FEATURE:
<223> OTHER INFORMATION: synthetic oligonucleotide

<400> SEQUENCE: 11
ggacgggaat caaggtaacg                                           20
```